US010557856B2

(12) United States Patent
Singbartl et al.

(10) Patent No.: US 10,557,856 B2
(45) Date of Patent: *Feb. 11, 2020

(54) BIOMARKERS OF RENAL INJURY

(75) Inventors: Kai Singbartl, Pittsburgh, PA (US); John A. Kellum, Jr., Pittsburgh, PA (US)

(73) Assignee: University Of Pittsburgh-Of The Commonwealth System Of Higher Education, Pittsburgh, PA (US)

( * ) Notice: Subject to any disclaimer, the term of this patent is extended or adjusted under 35 U.S.C. 154(b) by 460 days.

This patent is subject to a terminal disclaimer.

(21) Appl. No.: 13/235,005

(22) Filed: Sep. 16, 2011

(65) Prior Publication Data

US 2012/0077690 A1    Mar. 29, 2012

Related U.S. Application Data

(60) Provisional application No. 61/386,230, filed on Sep. 24, 2010.

(51) Int. Cl.
*G01N 33/68* (2006.01)

(52) U.S. Cl.
CPC .................. *G01N 33/6893* (2013.01)

(58) Field of Classification Search
None
See application file for complete search history.

(56) References Cited

U.S. PATENT DOCUMENTS

| | | | |
|---|---|---|---|
| 5,480,792 A | 1/1996 | Buechler et al. | 435/6.16 |
| 5,525,524 A | 6/1996 | Buechler et al. | 436/518 |
| 5,571,698 A | 11/1996 | Ladner et al. | 435/69.7 |
| 5,631,171 A | 5/1997 | Sandstorm et al. | 436/518 |
| 5,679,526 A | 10/1997 | Buechler et al. | 435/7.1 |
| 5,824,799 A | 10/1998 | Buechler et al. | 540/124 |
| 5,851,776 A | 12/1998 | Valkirs | 435/7.1 |
| 5,885,527 A | 3/1999 | Buechler | 422/58 |
| 5,922,615 A | 7/1999 | Nowakowski et al. | 436/518 |
| 5,939,272 A | 8/1999 | Buechler et al. | 435/7.1 |
| 5,947,124 A | 9/1999 | Buechler et al. | 128/898 |
| 5,955,377 A | 9/1999 | Maul et al. | 436/518 |
| 5,985,579 A | 11/1999 | Buechler et al. | 435/7.1 |
| 6,019,944 A | 2/2000 | Buechler | 422/58 |
| 6,057,098 A | 5/2000 | Buechler et al. | 435/6 |
| 6,113,855 A | 9/2000 | Buechler | 422/58 |
| 6,143,576 A | 11/2000 | Buechler | 436/518 |
| 6,350,571 B1 | 2/2002 | Lokeshwar et al. | 435/4 |
| 2009/0239242 A1 | 9/2009 | Kilty et al. | |
| 2010/0081148 A1 | 4/2010 | Singbartl et al. | |

FOREIGN PATENT DOCUMENTS

| WO | WO 2010059996 A1 * | 5/2010 | |
|---|---|---|---|
| WO | WO 2011025917 A1 * | 3/2011 | |
| WO | WO 2011075744 A1 * | 6/2011 | |
| WO | WO-2011075744 A1 * | 6/2011 | G01N 33/6893 |

OTHER PUBLICATIONS

Siew et al. Urine neutrophil gelatinase-associated lipocalin moderately predicts acute kidney injury in critically ill adults. Journal of the American Society of Nephrology. 20(8): 1823-32, published online Jul. 23, 2009.*
Waqar et al. Charlson's co-morbidity index predicts outcome of AKI in critically ill. Journal of the American Society of Nephrology. 20: Abstract TH-PO027, Oct. 2009.*
Waqar et al. et al. Charlson's co-morbidity index predicts outcome of AKI in critically ill. Journal of the American Society of Nephrology. 20: Abstract TH-PO027, Oct. 2009.*
Turney et al. Hyaluronic acid in end-stage renal failure treated by haemodialysis: clinical correlates and implications. . . Nephrology Dialysis Transplantation. 6(8):566-70, 1991.*
Stenvinkel et al. High serum hyaluronan indicates poor survival in renal replacement therapy. American Journal of Kidney Disease, 1999; 34(6):1083-8 (Year: 1999).*
Sano et al., "Localization and roles of CD44, hyaluronic acid and osteopontin in IgA nephropathy" *Nephron* 89:416-421 (2001).
Spurgeon et al., "Transforming growth factor-beta in acute renal failure: receptor expression, effects on proliferation, cellularity, and vascularization after recovery from injury," *Am. J. Physiol Renal Physiol.* 288:568-577 (2005).
Tengblad, "Affinity chromatography on immobilized hyaluronate and its application to the isolation of hyaluronate binding proteins from cartilage," *Biochem. Biophys. Acta*, 578: 281-289 (1979).
Wolf G., "Renal injury due to renin-angiotensin-aldosterone system activation of the transforming growth factor-beta pathway," *Kidney Int* 70:1914-1919 (2006).
Yarmush et al., "Coupling of antibody-binding fragments to solid-phase supports: site-directed binding of F(ab')$_2$ fragments," *J. Biochem. Biophys. Methods* 25:85-97 (1992).
Ali et al., "Incidence and outcomes in acute kidney injury: a comprehensive population-based study," *J Am Soc Nephrol* 18:1292-1298 (2007).
Bagshaw et al., "A multi-centre evaluation of the rifle criteria for early acute kidney injury in critically ill patients," *Nephrol. Dial. Transplant.* 23:1203-1210 (2008).
Bellomo et al., "Acute renal failure—definition, outcome measures, animal models, fluid therapy and information technology needs: the second international consensus conference of the acute dialysis quality initiative (ADQI)," Group*Crit Care* 8(4):R204-212 (2004).

(Continued)

*Primary Examiner* — Vanessa L. Ford
*Assistant Examiner* — Sandra E Dillahunt
(74) *Attorney, Agent, or Firm* — Medlen & Carroll, LLP

(57) ABSTRACT

This invention is related to the field of the prevention and treatment of kidney disease. The treatment of kidney disease may be tailored depending upon the need for, or expectation of, long-term dialysis. For example, prediction of long-term dialysis treatment can be determined by monitoring urine biomarkers related to the development of chronic kidney disease. For example, a normalized time course of approximately fourteen Days measuring hyaluronic acid, death receptor 5, and/or transforming growth factor β1 can be used to establish the risk of recovery versus non-recovery in patient's having suffered an acute kidney injury.

14 Claims, 7 Drawing Sheets

(56) References Cited

OTHER PUBLICATIONS

Bitter and Muir, "A modified uronic acid carbazole reaction," *Anal. Biochem.*, 4:330-334 (1962).
Chertow et al., "Acute kidney injury, mortality, length of stay, and costs in hospitalized patients," *J Am Soc Nephrol* 16:3365-3370 (2005).
Csoka et al., "Hyaluronidases in tissue invasion," *Invasion Metastasis*, 17:297-311 and 55 (1997).
Cwirla et al., "Peptides on phage: A vast library of peptides for identifying ligands," *Proc. Natl. Acad. Sci. USA* 87: 6378-6382 (1990).
Delpech et al., "Hyaluronan: fundamental principles and applications in cancer," *J Intern Med* 242: 41-48 (1997).
Devlin et al., "Random peptide libraries: a source of specific protein binding molecules," *Science* 249:404-406 (1990).
Dygert et al., "Determination of reducing sugars with improved precision," *Anal. Biochem.*, 13: 367-374 (1965).
Fischer et al., A readers' guide to the interpretation of diagnostic test properties: clinical example of sepsis, *Intensive Care Med.* 29:1043-1051 (2003).
Fosang et al., "An elisa plate based assay for hyaluronan using biotinylated proteoglycan G1 domain (HA-binding region),"*Matrix* 10:306-313 (1990).
Gold, "Purification and properties of hyaluronidase from human liver," *Biochem. J.*, 205: 69-74 (1982).
Hansell et al., "Hyaluronan content in the kidney in different states of body hydration," *Kidney Int* 58:2061-2068 (2000).
Hobarth et al., "Topical chemo-prophylaxis of superficial bladder cancer by mitomycin C and adjuvant hyaluronidase," *Eur. Urol.*, 21: 206-210 (1992).
Kellum, "Acute kidney injury," *Crit. Care Med.*, 36: S141-45 (2008).
Knudson et al., "The role and regulation of tumor associated hyaluronan," In: The Biology of Hyaluronan (J. Whelan, ed.), pp. 150-169, New York, Wiley Chichister (Ciba Foundation Symposium 143), 1989[1].
Lassnigg et al., "Minimal changes of serum creatinine predict prognosis in patients after cardiothoracic surgery: a prospective cohort study," *J Am Soc Nephrol* 15:1597-1605 (2004).
Laurent et al., "Hyaluronan," *FASEB J* 6:2397-2404 (1992).
Lewington et al., "Expression of CD44 in kidney after acute ischemic injury in rats," *Am J Physiol Regul Integr Comp Physiol* 278:R247-254 (2000).
Lin et al., "A hyaluronidase activity of the sperm plasma membrane protein PH-20 enables sperm to penetrate the cumulus layer surrounding the egg," *J. Cell Biol.*, 125: 1157-1163 (1995).
Lin et al., "Urinary hyaluronic acid is a Wilms' tumor marker", *J. Ped. Surg.*, 30: 304-308 (1995).
Lokeshwar et al., "Ankyrin binding domain of CD44(GP85) is required for the expression of hyaluronic acid-mediated adhesion function", *J. Cell Biol.*, 126 1099-1109 (1994).
Lokeshwar et al., "Bladder Tumor Markers for Monitoring Recurrence and Screening Comparison of Hyaluronic Acid—Hyaluronidase and BTA-Stat Tests", *Cancer* 95:61-72 (2002).
Lokeshwar et al., "Urinary hyaluronic acid and hyaluronidase: markers for bladder cancer detection and evaluation of grade", *J Urol*, 163:348-356 (2000).
Lokeshwar VB, Selzer MG., "Differences in hyaluronic acid mediated functions and signaling in arterial, microvessel, and vein-derived human endothelial cells", *J Biol Chem*, 275:27641-27649 (2000).
McCollough et al., "Contrast-Induced Nephropathy (CIN) Consensus Working Panel: Executive Summary," *Rev Cardiovasc Med.* 7(4):177-197 (2006).
McCormick and Zetter, "Adhesive interactions in angiogenesis and metastasis", *Pharmacol. Ther.*, 53: 239-260 (1992).
Mehta et al., "Acute kidney injury network: report of an initiative to improve outcomes in acute kidney injury," *Crit. Care* 11:R31 8 pages (2007).

Melin et al., "Ischemia-induced renal expression of hyaluronan and CD44 in diabetic rats", *Nephron Exp Nephrol* 103:e86-94 (2006).
Nelson et al., "A computer program for calculating antibody affinity constants," *Comput. Methods Programs Biomed.* 27: 65-68 (1988).
Okajima K., "Regulation of inflammatory responses by natural anticoagulants" *Immunol Rev* 184:258-274 (2001).
Palevsky et al., "Intensity of renal support in critically ill patients with acute kidney injury" *N Engl J Med* 359:7-20 (2008).
Pecoits-Filho et al., "Associations between circulating inflammatory markers and residual renal function in CRF patients", *Am J Kidney Dis.* 41(6):1212-1218 (2003).
Praught et al., "Are small changes in serum creatinine an important risk factor?," *Curr Opin Nephrol Hypertens* 14:265-270 (2005).
Ricci et al., "The rifle citeria and morality in acute kidney injury: a systematic review," *Kidney Int.* 73, 538-546 (2008).
Roden et al., Enzymatic pathways of hyaluronan catabolism. In: The Biology of hyaluronan, (J. Whelan, ed.), pp. 60-86, New York, Wiley Chichister (Ciba Foundation Symposium 143), 1989[2].
Sakurai et al., "An in vitro tubulogenesis system using cell lines derived from the embryonic kidney shows dependence on multiple soluble growth factors", *Proc Natl Acad Sci USA*, 94:6279-6284 (1997).
Sano et al., "Localization and roles of CD44, hyaluronic acid and osteopontin in IgA nephropath" *Nephron* 89:416-421 (2001).
Sattar et al., "Does hyaluronan have a role in endothelial cell proliferation of the synovium?" *Semin Arthritis Rheum* 22:37-43 (1992).
Scott et al., "Searching for peptide ligand with an epitope library," *Science* 249:386-388 (1990).
Shetty et al., "Tumor necrosis factor-related apoptosis inducing ligand (TRAIL) up-regulates death receptor 5 (DR5) mediated by NFkB activation in epithelial cell lines," *Apoptosis* 7:413-420 (2002).
Sibalic et al., "Upregulated renal tubular CD44, hyaluronan, and osteopontin in kdkd mice with interstitial nephritis," *Nephrol Dial Transplant* 12:1344-1353 (1997).
Stern et al., "Hyaluronidase levels in urine from Wilms' tumor patients,", *J. Natl. Canc. Inst.*, 83: 1569-1574 (1991).
Takeda et al., "Death receptor 5 mediated-apoptosis contributes to cholestatic liver disease," *Proc Natl Acad Sci USA*, 105:10895-10900 (2008).
Tengblad, "Affinity chromatography on immobilized hyaluronate and its application to the isolation of hyaluronate binding proteins from cartilage," *Biochim. Biophys. Acta*, 578: 281-289 (1979).
Uchino et al., "Acute renal failure in critically ill patients: a multinational, multicenter study," *JAMA* 294:813-818 (2005).
van Erp et al., "Application of a sol particle immunoassay to the determination of affinity constants of monoclonal antibodies," *J. Immunoassay* 12:425-443 (1991).
Wang et al., "Over-expression of C/EBP-alpha induces apoptosis in cultured rat hepatic stellate cells depending on p53 and peroxisome proliferator-activated receptor-gamma," *Biochem Biophys Res Commun* 380:286-291 (2009).
Ward et al., "Binding activities of a repertoire of single immunoglobulin variable domainssecreted from *Escherichia coil,*" *Nature* 341:544-546 (1989).
West et al., "Angiogenesis induced by degradation products of hyaluronic acid," *Science*, 228: 1324-1326 (1985).
Wilson et al., "Simplified conjugation chemistry for coupling peptides to F( ab') fragments: autologous red cell agglutination assay for HIV-1 antibodies," *J. Immunol. Methods* 175:267-273 (1994).
Wolf G., "Renal injury due to renin-angiotensin-aldosterone system activation of the transforming growth factor-beta pathway," *Kidney Int* 70:1914-1917 (2006).
Yang et al., "Dissection of key events in tubular epithelial to myofibroblast transition and its implications in renal interstitial fibrosis," *Am J Pathol* 159:1465-1475 (2001).
Yarmush et al., "Coupling of antibody-binding fragments to solid-phase supports: site-directed binding of F(ab')$_2$ fragments," *J. Biochem. Biophys. Methods* 25:85-97 (1992); and.
Zhu et al., "Molecular cloning of a mammalian hyaluronidase reveals identity with hemopexin, a serum heme-binding protein," *J. Biol. Chem.*, 269: 32092-32097 (1994).

(56) References Cited

OTHER PUBLICATIONS

Herrera et al., "Exogenous mesenchymal stem cell localize to the kidney by means of CD44 following acute tubular injury," *Kidney Intern.* 72: 430-441 (2007).
Levey et al., "Definition and classification of chronic kidney disease: A position statement from kidney disease: improving global outcomes (KDIGO)," *Kidney Int.* 67:2089-2100 (2005).
Lipkin et al., "Hyaluronic acid metabolism and its clinical significance in patients treated by continuous ambulatory peritoneal dialysis," *Nephrol Dial Transplant* 8:357-360 (1993).
Srisawat et al., "Recovery from acute kidney injury: determinants and predictors," *Contrib. Nephrol.* 165:284-291 (2010)[3].
Spurgeon et al., "Transforming growth factor-beta in acute renal failure: receptor expression, effects on proliferation, cellularity, and vascularization after recovery from injury," *Am. J. Physiol Renal Physiol.* 288:568-577 (2005); and.
Venkataraman et al., "Defining acute renal failure, the rifle criteria," *J. Intensive Care Med.*, 22:187-193 (2007).

\* cited by examiner

BIOMARKERS OF RENAL INJURY

This application for patent under 35 U.S.C. § 111(a) claims priority to Provisional Application(s) Ser. No. 61/386,230 filed on Sep. 24, 2010 under 35 U.S.C. § 111(b).

STATEMENT OF GOVERNMENTAL SUPPORT

This invention was made with government support under grant number DK070910 awarded by the National Institutes of Health. The government has certain rights in the invention.

FIELD OF INVENTION

This invention is related to the field of the prevention and treatment of kidney disease. The treatment of kidney disease may be tailored depending upon the need for, or expectation of, long-term dialysis. For example, prediction of long-term dialysis treatment can be determined by monitoring urine biomarkers related to the development of chronic kidney disease. For example, a normalized time course of approximately fourteen Days measuring hyaluronic acid, death receptor 5, and/or transforming growth factor β1 can be used to establish the risk of recovery versus non-recovery in patient's having suffered an acute kidney injury.

BACKGROUND

Chronic kidney disease (CKD) is believed to be one of the biggest and fastest growing health concerns facing the developed world. In the US alone, 26 million people have CKD and another 20 million more are at increased risk. CKD leads to dialysis and heart disease such that the associated medical costs total in the billions of dollars. A major cause of CKD is acute kidney injury (AKI), which is also associated with substantially increased healthcare costs, especially if dialysis (or a related kidney support technique) is required.

Chronic kidney disease can develop as a result of many different factors, but most notably, genetic predisposition and/or acute kidney injury. The degree of kidney injury is also associated with an incremental increase in long-term mortality. For example, fatalities occurring within one year after hospital discharge can be as high as 64% for patients with severe, dialysis-requiring AKI. Moreover, currently used markers of kidney function/injury, such as serum creatinine levels, are poor at discriminating long-term outcome of kidney disease. Regardless of the initiating factor, chronic kidney disease has a high proportion of patients requiring long-term dialysis (i.e., for example, renal replacement therapy or RRT). This treatment is expensive, time consuming, and can result in untoward side effects, including, but not limited to, blood vessel stenosis and/or thrombosis.

Thus, development of a biomarker that allows early identification and subsequent stratification of patients with AKI and also predicts recovery of kidney function, is a clinical tool having great need in the art.

SUMMARY

This invention is related to the field of the prevention and treatment of kidney disease. The treatment of kidney disease may be tailored depending upon the need for, or expectation of, long-term dialysis. For example, prediction of long-term dialysis treatment can be determined by monitoring urine biomarkers related to the development of chronic kidney disease. For example, a normalized time course of approximately fourteen Days measuring hyaluronic acid, death receptor 5, and/or transforming growth factor β1 can be used to establish the risk of recovery versus non-recovery in patient's having suffered an acute kidney injury.

In one embodiment, the present invention contemplates methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers of the present invention.

In one embodiment, the present invention contemplates a method comprising: a) providing; i) a patient exhibiting at least one symptom of an acute renal injury; and ii) a biological fluid sample obtained from the patient, wherein the sample comprises at least one renal biomarker; b) measuring a patient value comprising the at least one renal biomarker value in the sample; and c) predicting the probability of renal recovery for the patient based upon the patient value. In one embodiment, the renal recovery is predicted to occur within at least sixty Days from the onset of the acute renal injury. In one embodiment, the sample is obtained within at least fourteen Days from the onset of renal injury. In one embodiment, the sample is obtained within one Day from the onset of renal injury. In one embodiment, the predicting comprises correlating the patient value with a threshold value. In one embodiment, the predicting threshold value comprises a urinary hyaluronic acid value. In one embodiment, the urinary hyaluronic acid predicting threshold value is approximately 12 µg/mg of creatinine. In one embodiment, the predicting threshold value for the urinary hyaluronic acid value comprises an area under the receiver operating characteristic curve (AUC ROC) value of at least 0.70. In one embodiment, the predicting threshold value comprises a hyaluronic acid value and at least one clinical indicia value. In one embodiment, the predicting threshold value for the urinary hyaluronic acid value and the at least one clinical indicia value comprises an area under the receiver operating characteristic curve (AUC ROC) value of at least 0.75. In one embodiment, the predicting threshold value comprises a urinary transforming growth factor β1 value. In one embodiment, the predicting threshold value for the urinary transforming growth factor β1 value is approximately 274 pg/mg of creatinine. In one embodiment, the predicting threshold value for transforming growth factor β1 value comprises an area under the receiver operating characteristic curve (AUC ROC) value of at least 0.70. In one embodiment, the predicting threshold value comprises the urinary transforming growth factor β1 value and at least one clinical indicia value. In one embodiment, the predicting threshold value for the urinary transforming growth factor β1 and at least one clinical indicia value comprises an area under the receiver operating characteristic curve (AUC ROC) value of at least 0.74. In one embodiment, the predicting threshold value comprises a urinary death receptor 5 value. In one embodiment, the predicting threshold value for the urinary death receptor 5 value is approximately 2.7 ng/mg of creatinine. In one embodiment, the predicting threshold value for the urinary death receptor 5 value comprises an area under the receiver operating characteristic curve (AUC ROC) value of at least 0.70. In one embodiment, the predicting threshold value comprises the urinary death receptor 5 value and a clinical indicia value. In one embodiment, the predicting threshold value for the urinary death receptor 5 value and the at least one clinical indicia value comprises an area under the receiver operating characteristic curve (AUC ROC) value of at least 0.76. In one embodiment, the predicting threshold value comprises at least one clinical indicia value. In one embodiment, the clinical indica value is selected from the group comprising age, SOFA score, Charlson comorbidity index, or APACHE II score. In one embodiment, the at least one clinical indicia value comprises an area under the receiver operating characteristic curve (AUC ROC) value of at least 0.71. In one embodiment, the patient value comprises at least two clinical indicia values. In one embodiment, the at least two clinical indicia values comprises a combined area under the receiver operating characteristic curve (AUC ROC) value of at least 0.74. In one embodiment, the at least two clinical indica values comprise age and Charlson comorbidity index.

In one embodiment, the present invention contemplates a method for evaluating renal status that identifies a risk stratification of a subject comprising: a) providing; i) a patient exhibiting at least one symptom of an acute renal injury; ii) a biological fluid sample obtained from the patient, wherein said sample comprises at least one renal biomarker; b) measuring a patient value comprising the at least one renal biomarker value in the sample; and c) correlating the patient value with a threshold biomarker value wherein a risk stratification is identified. In one embodiment, the correlating further identifies a positive going renal biomarker value. In one embodiment, the correlating further identifies a negative going renal biomarker marker value. In one embodiment, the patient value comprises a urinary hyaluronic acid value and at least one clinical indicia value. In one embodiment, the patient value comprises a transformation growth factor $\beta 1$ value. In one embodiment, the patient value comprises a death receptor 5 value. In one embodiment, the patient value further comprises at least one clinical indicia value. In one embodiment, the sample is obtained within at least fourteen Days from the onset of the acute renal injury. In one embodiment, the risk stratification comprises a modified Risk, Injury, Failure, Loss (RIFLE) criteria selected from the group comprising Stage I, Stage II, or Stage III.

In one embodiment, the Stage I comprises a Risk category. In one embodiment, the Stage II comprises an Injury category. In one embodiment, the Stage III comprises a Failure category. In one embodiment, the risk stratification comprises assigning a likelihood of renal recovery. In one embodiment, the likelihood of renal recovery comprises the biomarker value having an area under the receiver operating characteristic curve (AUC ROC) above the threshold value of approximately 0.70. In one embodiment, the risk stratification comprises assigning a likelihood of the renal non-recovery. In one embodiment, the likelihood of renal non-recovery comprises the biomarker value having an area under the receiver operating characteristic curve (AUC ROC) below the threshold value of approximately 0.70. In one embodiment, the risk stratification comprises determining a patient clinical outcome risk. In one embodiment, the clinical outcome risk comprises an improvement in renal function. In one embodiment, the clinical outcome risk comprises a reduced renal function. In one embodiment, the reduced renal function comprises renal injury. In one embodiment, the renal injury is progressive. In one embodiment, the clinical outcome risk comprises a Loss category. In one embodiment, the clinical outcome risk comprises an End Stage Renal Failure category. In one embodiment, the likelihood of the occurrence of the clinical outcome risk is correlated to the patient value area under the receiver operating characteristic (AUC ROC) curve. In one embodiment, the likelihood of the Loss category increases within an AUC ROC value ranging between approximately 0.5-0.3. In one embodiment, the likelihood of the Loss category decreases above an AUC ROC value of 0.5. In one embodiment, the likelihood of the End Stage Renal Failure category increased below an AUC ROC value of 0.3. In one embodiment, the likelihood of the End Stage Renal Failure category decreases above an AUC ROC value of approximately 0.3. In one embodiment, the risk stratification comprises determining a subject risk for future reduced renal function. In one embodiment, the subject risk for future reduced renal function increases below an AUC ROC value 0.5. In one embodiment, the subject risk for future reduced renal function decreases above an AUC ROC value of 0.5. In one embodiment, the future reduced renal function is likely to occur within 180 Days of the time at which the body fluid sample is obtained from the subject. In one embodiment, the future reduced renal function is likely to occur within a time period selected from the group comprising 18 months, 120 Days, 90 Days, 60 Days, 45 Days, 30 Days, 21 Days, 14 Days, 7 Days, 5 Days, 96 hours, 72 hours, 48 hours, 36 hours, 24 hours, 12 hours, or less. In one embodiment, the reduced renal function occurs at 0 hours of the time at which the body fluid sample is obtained from the subject, thereby providing a diagnosis of a current condition.

In one embodiment, the present invention contemplates a method comprising: a) providing a subject comprising at least one pre-existing risk factor for a renal disease; and b) selecting the subject for a risk stratification based on the at least one renal disease pre-existing risk factor. In one embodiment, the pre-existing risk factor comprises a renal biomarker. In one embodiment, the renal biomarker is selected from the group comprising urinary hyaluronic acid, urinary transformation growth factor $1\beta$, or urinary death receptor 5. In one embodiment, the risk stratification comprises a modified Risk, Injury, Failure, Loss (RIFLE) criteria selected from the group comprising Stage I, Stage II, or Stage III. In one embodiment, the Stage I comprises a Risk category. In one embodiment, the Stage II comprises an Injury category. In one embodiment, the Stage III comprises a Failure category. In one embodiment, the risk stratification comprises a Failure category. In one embodiment, the risk stratification comprises an End Stage Renal Disease category. In one embodiment, the Risk category comprises an AUC ROC value ranging between approximately 0.6-0.7. In one embodiment, the Injury category comprises an AUC ROC value ranging between approximately 0.5-0.6. In one embodiment, the Failure category comprises an AUC ROC value ranging between approximately 0.4-0.5. In one embodiment, the Loss category comprises an AUC ROC value ranging between approximately 0.3-0.4. In one embodiment, the End Stage Renal Disease category comprises an AUC ROC value below 0.3. In one embodiment, the renal disease is selected from the group comprising prerenal disease, intrinsic renal disease, or postrenal acute renal failure disease. In one embodiment, the subject further comprises at least one medical condition selected from the group comprising undergoing or have undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis. In one embodiment, the subject further comprises exposure to at least one compound selected from the group comprising non-steriodial anti-inflammatory drugs, cyclosporines, tacrolimus, aminoglycosides, foscarnet, ethylene glycol, hemoglobin, myoglobin, ifosfamide, heavy metals, methotrexate, radiopaque contrast agents, or streptozotocin. In one embodiment, the subject is selected for risk stratification based on an existing diagnosis of an injury selected from the group comprising renal function, reduced renal function, or acute renal failure.

In one embodiment, the present invention contemplates a method for diagnosing a renal injury in a subject. In one embodiment, the method further comprises evaluating a renal status to assess whether or not a subject has suffered from an injury to renal function, reduced renal function, or ARF. In these embodiments, the assay measurement, for example a measured concentration of HA, DR5, and/or TGFβ1, is/are correlated to the occurrence or nonoccurrence of a change in renal status. In one embodiment, a diagnostic method comprises diagnosing the occurrence or nonoccurrence of an injury to renal function. In one embodiment, the assay measurement is/are correlated to the occurrence or nonoccurrence of such an injury. In one embodiment, the diagnostic method comprises diagnosing the occurrence or non-occurrence of reduced renal function. In one embodiment, the assay measurement is/are correlated to the occurrence or non-occurrence of an injury causing reduced renal function. In one embodiment, the diagnostic method comprises diagnosing the occurrence or non-occurrence of ARF. In one embodiment, the assay measurement is/are correlated to the occurrence or nonoccurrence of an injury causing ARF. In one embodiment, the diagnostic method comprises diagnosing a subject as being in need of renal replacement therapy. In one embodiment, the assay measurement is/are correlated to a need for renal replacement therapy. In one embodiment, the diagnostic method comprises diagnosing a subject as being in need of renal transplantation. In one embodiment, the assay measurement is/are correlated to a need for renal transplantation.

In one embodiment, each of the measured concentration(s) may be compared to a threshold value. In one embodiment, the measured concentration(s) may each be compared to a threshold value, wherein either a "positive going kidney injury marker", or a "negative going kidney injury marker" is identified.

In one embodiment, the present invention contemplates a method comprising monitoring a renal status in a subject. In one embodiment, the monitoring correlates to an occurrence or a non-occurrence of a change in renal status in the subject. In one embodiment, the renal status is reduced. In one embodiment, the subject is suffering from a renal function injury. In one embodiment, the subject is suffering from acute renal failure. In one embodiment, the subject is at risk of an injury to renal function due to the pre-existence of one or more known risk factors for prerenal, intrinsic renal, or postrenal ARF. In one embodiment, the measured concentration(s) may be compared to a threshold value. In one embodiment, the measured concentration(s) may each be compared to a threshold value, wherein either a "positive going kidney injury marker", or a "negative going kidney injury marker" is identified.

In one embodiment, the present invention contemplates a method for classifying a renal injury in a subject. In one embodiment, the method comprises evaluating a renal status in the subject. In one embodiment, the renal status determines a renal injury selected from the group comprising prerenal, intrinsic renal, or postrenal. In one embodiment, the renal status determines renal injury selected from the group comprising acute tubular injury, acute glomerulonephritis acute tubulointerstitial nephritis, acute vascular nephropathy, or infiltrative disease. In one embodiment, the renal status assigns a likelihood that the subject will progress to a particular RIFLE stage. In one embodiment, the assay measurement, for example in a measured concentration of HA, DR5, and/or TGFβ1. In one embodiment, the measured concentration is/are correlated to a particular injury classification and/or injury subclassification. In one embodiment, the measured concentration may be compared to a threshold value. In one embodiment, the measured concentration is above the threshold, wherein a particular classification is assigned. In one embodiment, the measured concentration is below the threshold, wherein a different classification may be assigned.

In one embodiment, the present invention contemplates a method, comprising a) providing; i) a patient, wherein the patient exhibits an acute kidney injury; ii) at least two urine samples derived from the patient; b) detecting persistently elevated hyaluronic acid in the urine samples; c) predicting the patient to require long-term dialysis. In one embodiment, wherein the samples are collected on the first and fourteenth Day after initiation of replacement therapy for severe kidney injury. In one embodiment, the method further comprises diagnosing the patient with chronic kidney disease. In one embodiment, the diagnosing occurs at least sixty Days after the kidney injury. In one embodiment, the method further comprises entering the patient in a chronic kidney disease prevention program.

In one embodiment, the present invention contemplates a method, comprising a) providing; i) a patient, wherein the patient exhibits an acute kidney injury, wherein the patient is at risk for development of chronic kidney disease; ii) at least two urine samples derived from the patient; b) detecting persistently elevated hyaluronic acid in the urine samples; c) treating the patient to prevent chronic kidney disease. In one embodiment, the treating is initiated on Day 14 after the kidney disease.

In one embodiment, the present invention contemplates a method comprising: a) providing; i) a patient having suffered an acute kidney injury; ii) obtaining a plurality of urinary hyaluronic acid and creatinine levels from the patient, wherein the levels are obtained over time; b) constructing a urinary hyaluronic acid level time course, wherein the time course is normalized against the urinary creatinine levels; and c) predicting chronic kidney disease development. In one embodiment, wherein the predicting includes long-term renal replacement therapy (i.e., for example, dialysis).

Definitions

As used herein, an "injury to renal function" is an abrupt (i.e., for example, within 14 Days, preferably within 7 Days, more preferably within 72 hours, and still more preferably within 48 hours) measurable reduction in a measure of renal function. Such an injury to renal function may be identified, for example, by a decrease in glomerular filtration rate (GFR) or estimated GFR (eGFR), a reduction in urine output, an increase in serum creatinine, an increase in serum cystatin C, a requirement for renal replacement therapy (i.e., for example, dialysis), etc.

As used herein, an "improvement in renal function" is an abrupt (i.e., for example, within 14 Days, preferably within 7 Days, more preferably within 72 hours, and still more preferably within 48 hours) measurable increase in a measure of renal function. Preferred methods for measuring and/or estimating GFR are described hereinafter.

As used herein, "reduced renal function" is an abrupt (i.e., for example, within 14 Days, preferably within 7 Days, more preferably within 72 hours, and still more preferably within 48 hours) reduction in kidney function identified by an absolute increase in serum creatinine of greater than or equal to 0.1 mg/dL (≥8.8 μmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (i.e., for example, within 14 Days, preferably within 7 Days, more preferably within 72 hours, and still more preferably within 48 hours) reduction in kidney function identified by an absolute increase in serum creatinine of greater than or equal to 0.3 mg/dl (≥26.4 μmol/l), a percentage increase in scram creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

As used herein, the term "relating a signal to the presence or amount" of an analyte refers to assay measurements using a standard curve calculated with known concentrations of the analyte of interest. The skilled artisan will understand that the signals obtained from an assay are often a direct result of complexes formed between, for example, one or more antibodies and a target biomolecule (i.e., for example, an analyte) and/or polypeptides containing an epitope(s) to which, for example, antibodies bind. While such assays may detect a full length biomarker and the assay result may be expressed as a concentration of a biomarker of interest, the signal from the assay is actually a result of all such "immunoreactive" polypeptides present in the sample.

As the term is used herein, an assay is "configured to detect" an analyte if an assay can generate a detectable signal indicative of the presence or amount of a physiologically relevant concentration of the analyte. For example, an antibody epitope is usually on the order of 8 amino acids, such that an immunoassay can be configured to detect a marker of interest that will also detect polypeptides related to the marker sequence, so long as those polypeptides contain the epitope(s) necessary to bind to the antibody or antibodies used in the assay.

The term "related marker" as used herein with regard to a biomarker such as one of the renal biomarkers (i.e., for example, a kidney injury marker) described herein. A related marker may also refer to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "subject" or "patient" as used herein, refers to a human or non-human organism. Thus, the methods and compositions described herein are equally applicable to both human and veterinary disease. Further, while a subject or patient is preferably a living organism, the invention described herein may be used in post-mortem analysis as well. Preferred subjects or patients are humans, which as used herein refer to living humans that are receiving medical care for a disease or condition.

The term "analyte" as used herein, refers to any measured compound or molecule. Preferably, an analyte is measured in a sample (i.e., for example, a body fluid sample). Such a sample may be obtained from a subject or patient, or may be obtained from biological materials intended to be provided to the subject or patient. For example, a sample may be obtained from a kidney being evaluated for possible transplantation into a subject, such that an analyte measurement may be used to evaluate the kidney for preexisting damage.

The term "body fluid sample" as used herein, refers to any sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing medical condition or the effect of a treatment regimen on a medical condition. Preferred body fluid samples include but are not limited to, blood, serum, plasma, cerebrospinal fluid, urine, saliva, sputum, or pleural effusions. In addition, certain body fluid samples may be more readily analyzed following a fractionation or purification procedure, for example, separation of whole blood into serum or plasma components.

The term "diagnosis" as used herein, refers to methods by which trained medical personnel can estimate and/or determine the probability (i.e., for example, a likelihood) of whether or not a patient is suffering from a given disease or condition. In the case of the present invention, "diagnosis" includes correlating the results of an assay (i.e., for example, an immunoassay) for a renal biomarker of the present invention, optionally together with other clinical indicia, to determine the occurrence or nonoccurrence of an acute renal injury or acute renal failure for a subject or patient from which a sample was obtained and assayed. That such a diagnosis is "determined" is not meant to imply that the diagnosis is 100% accurate. Thus, for example, a measured biomarker level below a predetermined diagnostic threshold may indicate a greater likelihood of the occurrence of a disease in the subject relative to a measured biomarker level above the predetermined diagnostic threshold may indicate a lesser likelihood of the occurrence of the same disease.

The term "prognosis" as used herein, refers to a probability (i.e., for example, a likelihood) that a specific clinical outcome will occur. For example, a level or a change in level of a prognostic indicator, which in turn is associated with an increased probability of morbidity (e.g., worsening renal function, future ARF, or death) is referred to as being "indicative of an increased likelihood" of an adverse outcome in a patient.

The term "RIFLE" criteria, as used herein, refers to any quantitative clinical evaluation of renal status used to establish renal classifications of Risk, Injury, Failure, Loss, & End Stage Renal Disease based upon a uniform definition of acute kidney injury (AKI). Kellum, *Crit. Care Med.* 36: S141-45 (2008); and Ricci et al., *Kidney Int.* 73, 538-546 (2008), each hereby incorporated by reference in its entirety.

The term, "modified RIFLE criteria", as used herein, provide alternative classifications for stratifying AKI patients, and may include, Stage I, Stage II, and/or Stage III. Mehta et al., *Crit. Care* 11:R31 (2007), hereby incorporated by reference in its entirety.

The term, "Stage I", as used herein, refers to a risk stratification comprising a RIFLE Risk category, characterized by an increase in serum creatinine of more than or equal to 0.3 mg/dL (≥26.4 μmol/L) and/or an increase to more than or equal to 150% (1.5-fold) from baseline. Alternatively, the category may be defined by a urine output less than 0.5 mL/kg per hour for more than 6 hours.

The term, "Stage II", as used herein, refers a risk stratification comprising a RIFLE Injury category, characterized by an increase in serum creatinine to more than 200%

(>2-fold) from baseline. Alternatively, the category may be defined by a urine output less than 0.5 mL/kg per hour for more than 12 hours.

The term, "Stage III", as used herein, refers to a risk stratification comprising a RIFLE Failure category, characterized by an increase in serum creatinine to more than 300% (>3-fold) from baseline and/or serum creatinine ≥354 µmol/L accompanied by an acute increase of at least 44 µmol/L. Alternatively, the category may be defined by a urine output less than 0.3 mL/kg per hour for 24 hours or anuria for 12 hours.

The term "Risk category", as used herein, refers to a RIFLE classification wherein, in terms of serum creatinine, means any increase of at least 1.5 fold from baseline, or urine production of <0.5 ml/kg body weight/hr for approximately 6 hours.

The term "Injury category" as used herein includes, refers to a RIFLE classification wherein, in terms of serum creatinine, means any increase of at least 2.0 fold from baseline or urine production <0.5 ml/kg/hr for 12 h.

The term "Failure category" as used herein includes, refers to a RIFLE classification wherein, in terms of serum creatinine means any increase of at least 3.0 fold from baseline or a urine creatinine >355 µmol/l (with a rise of >44) or urine output below 0.3 ml/kg/hr for 24 h, or anuria for at least 12 hours.

The term "Loss category" as used herein, refers to a clinical outcome risk and/or a RIFLE classification wherein the clinical outcome risk is characterized by a persistent need for renal replacement therapy for more than four weeks.

The term "End Stage Renal Disease category" or "ESRD category" as used herein, refers to a clinical outcome risk and/or a RIFLE classification characterized by a need for dialysis for more than 3 months.

The term "clinical outcome risk" as used herein, refers to a medical prognosis directed towards either renal recovery or renal non-recovery.

The term "renal biomarker" as used herein, refers to any biological compound related to the progressive development of chronic kidney disease. In particular, a renal biomarker may be a kidney injury marker. For example, a renal biomarker may comprise hyaluronic acid, death receptor 5, transformation growth factor β1, or any of their metabolites and/or derivatives.

The term "positive going biomarker" as that term is used herein, refers to any biomarker that is determined to be elevated in subjects suffering from a disease or condition, relative to subjects not suffering from that disease or condition.

The term "negative going biomarker" as that term is used herein, refer to any biomarker that is determined to be reduced in subjects suffering from a disease or condition, relative to subjects not suffering from that disease or condition.

The term "positive going renal biomarker value" as used herein, refers to any increased likelihood (i.e., for example, increased probability) of suffering a future injury to renal function assigned to a subject when the measured biomarker concentration is above a specified threshold value, relative to a likelihood assigned when the measured biomarker concentration is below the specified threshold value. Alternatively, when the measured biomarker concentration is below a specified threshold value, an increased likelihood of a non-occurrence of an injury to renal function may be assigned to the subject relative to the likelihood assigned when the measured biomarker concentration is above the specified threshold value. Alternatively, when the measured biomarker concentration is below the threshold value, an improvement of renal function may be assigned to the subject. A positive going kidney injury marker may include, but not be limited to, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc.

The term "negative going renal biomarker value" as used herein, refers to any increased likelihood (i.e., for example, an increased probability) of suffering a future injury to renal function assigned to the subject when the measured biomarker concentration is below a specified threshold value, relative to a likelihood assigned when the measured biomarker concentration is above the threshold value. Alternatively, when the measured biomarker concentration is above the threshold value, an increased likelihood of a non-occurrence of an injury to renal function may be assigned to the subject relative to the likelihood assigned when the measured biomarker concentration is below the threshold value. Alternatively, when the measured biomarker concentration is above the threshold value, an improvement of renal function may be assigned to the subject. A negative going kidney injury marker may include, but not be limited to, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc.

The term "pre-existing" and "pre-existence" as used herein, means any risk factor (i.e., for example, a renal biomarker) existing at the time a body fluid sample is obtained from the subject.

The term "predicting" as used herein, refers to a method of forming a prognosis and/or a stratification risk assignment, wherein a medically trained person analyzes biomarker information, and optionally with relevant clinical indicia and/or demographic information.

The term "acute renal disease/failure/injury" as used herein, refers to any progressive worsening of renal function over hours to Days, resulting in the retention of nitrogenous wastes (such as urea nitrogen) and creatinine in the blood. Retention of these substances may also be referred to as, azotemia. In: Current Medical Diagnosis & Treatment 2008, 47th Ed, McGraw Hill, New York, pages 785-815, herein incorporated by reference in their entirety.

The term "chronic renal disease/failure/injury" as used herein, refers to a medical condition wherein exemplary symptoms may include, but are not limited to, hyperphosphatemia (i.e., for example, >4.6 mg/dl) or low glomerular filtration rates (i.e., for example, <90 ml/minute per 1.73 m$^2$ of body surface). However, many CKD patients may have normal serum phosphate levels in conjunction with a sustained reduction in glomerular filtration rate for 3 or more months, or a normal GFR in conjunction with sustained evidence of a structural abnormality of the kidney. In some cases, patients diagnosed with chronic kidney disease are placed on hemodialysis to maintain normal blood homeostasis (i.e., for example, urea or phosphate levels). Alternatively, "chronic kidney disease" refers to a medical condition wherein a patients has either i) a sustained reduction in GFR <60 ml/min per 1.73 m$^2$ of body surface for 3 or more months; or ii) a structural or functional abnormality of renal function for 3 or more months even in the absence of a reduced GFR. Structural or anatomical abnormalities of the kidney could be defined as, but not limited to, persistent microalbuminuria or proteinuria or hematuria or presence of renal cysts. Chronic renal failure (chronic kidney disease) may also result from an abnormal loss of renal function over months to years. In: Current Medical Diagnosis & Treatment 2008, 47th Ed, McGraw Hill, New York, pages 785-815, herein incorporated by reference in their entirety.

The term "about" as used herein in the context of any of any assay measurements refers to +/−5% of a given measurement.

The term "asymptomatic" as used herein, refers to a patient and/or subject that does not have a renal disease and/or injury, wherein a renal disease and/or injury symptom may include, but is not limited to, having a reduced glomerular filtration rate (i.e., for example, between approximately 70-89 ml/min per 1.73 m$^2$ of body surface) for less than three months.

The term "glomerular filtration rate" as used herein, refers to any measurement capable of determining kidney function. In general, a normal glomerular filtration rate ranges between approximately 120-90 ml/minute per 1.73 m$^2$ of body surface. Compromised kidney function is assumed when glomerular filtration rates are less than 90 ml/minute per 1.73 m$^2$ of body surface. Kidney failure is probable when glomerular filtration rates fall below approximately 30 ml/minute per 1.73 m$^2$ of body surface. Dialysis is frequently initiated when glomerular filtration rates fall below approximately 15 ml/minute per 1.73 m$^2$ of body surface.

The term "renal failure" as used herein, refers to any acute, sudden, and/or chronic loss of the ability of the kidneys to remove waste and concentrate urine without losing electrolytes.

The term "biological sample" as used herein, refers to any substance derived from a living organism. For example, a sample may be derived from blood as a urine sample, serum sample, a plasma sample, and or a whole blood sample. Alternatively, a sample may be derived from a tissue collected, for example, by a biopsy. Such a tissue sample may comprise, for example, kidney tissue, vascular tissue and/or heart tissue. A biological sample may also comprise body fluids including, but not limited to, urine, saliva, or perspiration.

The term "reagent" as used herein, refers to any substance employed to produce a chemical reaction so as to detect, measure, produce, etc., other substances.

The term "antibody" as used herein refers to any peptide or polypeptide derived from, modeled after, or substantially encoded by, an immunoglobulin gene or immunoglobulin genes, or fragments thereof, capable of specifically binding an antigen or epitope. See, e.g. In: Fundamental Immunology, 3rd Edition, W. E. Paul, ed., Raven Press, NY (1993); Wilson et al., *J. Immunol. Methods* 175:267-273 (1994); and Yarmush et al., *J. Biochem. Biophys. Methods* 25:85-97 (1992). The term antibody includes, but is not limited to, antigen-binding portions, i.e., "antigen binding sites" exemplified by fragments, subsequences, and/or complementarity determining regions (CDRs)) that retain capacity to bind antigen, including, but not limited to: (i) a Fab fragment, a monovalent fragment comprising $V_L$, $V_H$, $C_L$ or $CH_I$ domains; (ii) a F(ab')$_2$ fragment, a bivalent fragment comprising two Fab fragments linked by a disulfide bridge at the hinge region; (iii) a $F_d$ fragment comprising $V_H$ and $C_{H1}$ domains; (iv) a F, fragment comprising $V_L$ and $V_H$ domains of a single arm of an antibody, (v) a dAb fragment (Ward et al., *Nature* 341:544-546 (1989)), which comprises a $V_H$ domain; or (vi) an isolated complementarity determining region (CDR). Single chain antibodies are also included by reference in the term "antibody."

The term "epitope" as used herein, refers to any antigenic determinant capable of specific binding to an antibody. Epitopes usually display chemically active surface molecules such as amino acids or sugar side chains and usually have specific three dimensional structural characteristics, as well as specific charge characteristics. Conformational and nonconformational epitopes may be distinguished in that the binding to the former but not the latter can be lost in the presence of denaturing solvents.

The term "correlating" as used herein, in reference to the use of biomarkers, refers to comparing the presence and/or amount of any biomarker(s) in a patient to its presence and/or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

DETAILED DESCRIPTION OF THE INVENTION

Figure 1:
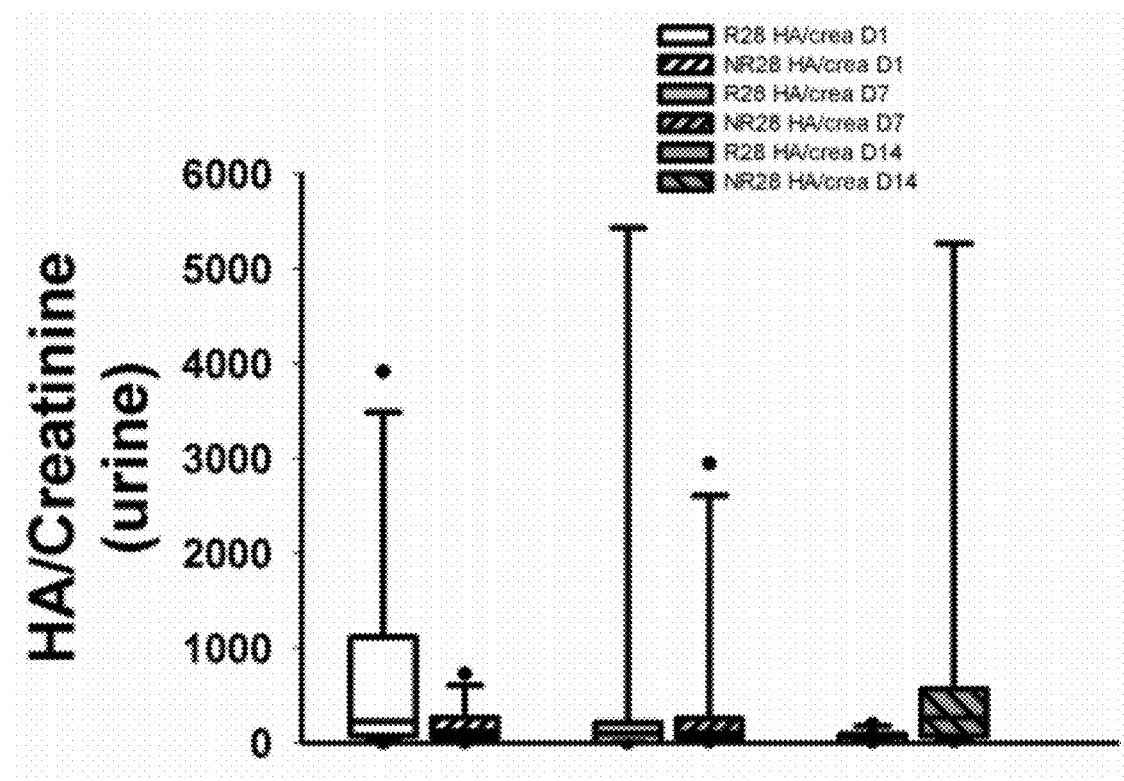
FIG. 1 presents exemplary data showing urine hyaluronic acid excretion normalized to urine creatinine in patients exhibiting acute kidney injury. Samples were taken between one-fourteen Days after initiation of replacement therapy for severe acute kidney injury (i.e., D1, D7 and D14). The data shown represent data in patients that were either recovering or not recovering twenty-eight Days after kidney injury (R28 and NR28, respectively).

This invention is related to the field of the prevention and treatment of kidney disease. The treatment of kidney disease may be tailored depending upon the need for, or expectation of, long-term dialysis. For example, prediction of long-term dialysis treatment can be determined by monitoring urine biomarkers related to the development of chronic kidney disease. For example, a normalized time course of approximately fourteen Days measuring hyaluronic acid, death receptor 5, and/or transforming growth factor β1 can be used to establish the risk of recovery versus non-recovery in patient's having suffered an acute kidney injury.

It has long been desired in the art that if research efforts to treat AKI and prevent CKD could be tailored according to long-term prognosis, a more effective clinical strategy could be implemented. Using such a method patients predicted to not recover kidney function could be selectively provided aggressive treatment. Conversely, patients with a favorable prognosis would be spared from more aggressive interventions and their potential adverse effects.

Various embodiments presented herein, have solved various problems in the art that have heretofore prevented the ability of clinicians to accurate predict which patients will recover, and which patient will not recover, from renal disease and/or injury.

I. Kidney Injury and/or Disease

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17th Ed., McGraw Hill, New York, pages 1741-1830, which are hereby incorporated by reference in their entirety. The kidneys are located in the flank (back of the upper abdomen at either side of the spinal column). They are deep within the abdomen and are protected by the spine, lower rib cage, and the strong muscles of the back. This location protects the kidneys from many external forces. They are well-padded for a reason—kidneys are highly vascular organs, which means that they have a large blood supply. If injury occurs, severe bleeding may result.

Kidneys may be injured by damage to the blood vessels that supply or drain them. This may be in the form of aneurysm, arteriovenous fistula, arterial blockage, or renal vein thrombosis. The extent of bleeding depends on the location and the degree of injury. Kidneys may also bleed profusely if they are damaged centrally (on the inside)—this is a life-threatening injury. Fortunately, most kidney injuries caused by blunt trauma occur peripherally, only causing bruising of the kidney (usually a self-limiting process).

People with undiagnosed kidney conditions—such as angiomyolipoma (benign tumor), ureteropelvic junction obstruction (congenital or acquired UPJ Obstruction), and other disorders—are more susceptible to kidney injuries and more likely to have serious complications if they occur. Other causes of kidney injury and bleeding are medical procedures. Kidney biopsies, nephrostomy tube placements, or other surgeries can cause an abnormal connection between an artery and vein (arteriovenous fistula). This is usually a self-limiting problem, but close observation is usually needed. Injury to the kidney can also disrupt the urinary tract, causing leakage of the urine from the kidney.

Each kidney filters about 1700 liters of blood per Day and concentrates fluid and waste products into about 1 liter of urine per Day. Because of this, the kidneys receive more exposure to toxic substances in the body than almost any other organ. Therefore, they are highly susceptible to injury from toxic substances. Analgesic nephropathy is one of the most common types of toxic damage to the kidney. Exposure to lead, cleaning products, solvents, fuels, or other nephrotoxic chemicals (those which can be toxic to the kidney) can damage kidneys. Excessive buildup of body waste products, such as uric acid (that can occur with gout or with treatment of bone marrow, lymph node, or other disorders) can also damage the kidneys.

Inflammation (irritation with swelling and presence of extra immune cells) caused by immune responses to medications, infection, or other disorders may also injure the structures of the kidney, usually causing various types of glomerulonephritis or acute tubular necrosis (tissue death). Autoimmune disorders may also damage the kidneys. Injury to the kidney may result in short-term damage with minimal or no symptoms. Alternately, it can be life-threatening because of bleeding and associated shock, or it may result in acute renal failure or chronic renal failure.

Ureteral injuries (injuries to the tubes which carry urine from the kidneys to the bladder) can also be caused by trauma (blunt or penetrating), complications from medical procedures, and other diseases in the retroperitoneum such as retroperitoneal fibrosis (RPF), retroperitoneal sarcomas, or metastatic lymph node positive cancers. Medical therapies (such as OB/GYN surgeries, prior radiation or chemotherapy, and previous abdominopelvic surgeries) increase the risk for ureteral injuries.

A. Acute Kidney Failure

Acute (sudden) kidney failure is the sudden loss of the ability of the kidneys to remove waste and concentrate urine without losing electrolytes. There are many possible causes of kidney damage including, but are not limited to, decreased blood flow, which may occur with extremely low blood pressure caused by trauma, surgery, serious illnesses, septic shock, hemorrhage, burns, or dehydration, acute tubular necrosis (ATN), infections that directly injury the kidney such as acute pyelonephritis or septicemia, urinary tract obstruction (obstructive uropathy), autoimmune kidney disease such as interstitial nephritis or acute nephritic syndrome, disorders that cause clotting within the thin blood vessels of the kidney, idiopathic thrombocytopenic thrombotic purpura (ITTP), transfusion reaction, malignant hypertension, scleroderma, hemolytic-uremic syndrome, disorders of childbirth, such as bleeding placenta abruptio or placenta previa Symptoms of acute kidney failure may include, but are not limited to, decrease in amount of urine (oliguria), urination stops (anuria), excessive urination at night, ankle, feet, and leg swelling, generalized swelling, fluid retention, decreased sensation, especially in the hands or feet, decreased appetite, metallic taste in mouth, persistent hiccups, changes in mental status or mood, agitation, drowsiness, lethargy, delirium or confusion, coma, mood changes, trouble paying attention, hallucinations, slow, sluggish, movements, seizures, hand tremor (shaking), nausea or vomiting, may last for Days, bruising easily, prolonged bleeding, nosebleeds, bloody stools, flank pain (between the ribs and hips), fatigue, breath odor, or high blood pressure.

Acute renal failure (ARF) may also be referred to as acute kidney injury (AKI) and may be characterized by an abrupt (i.e., for example, typically detected within about 48 hours to 1 week) reduction in glomerular filtration rate (GFR). This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in association with their respective risk factors are summarized below. See, Table 1; In: Merck Manual, 17th ed., Chapter 222, and which is hereby incorporated by reference in their entirety.

TABLE 1

Representative Acute Renal Failure Risk Factors

| Type of Renal Failure | Risk Factors |
|---|---|
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to Days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of Days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 Days, resolution within 1 week) rise in blood urea nitrogen and serum creatinine.

A commonly reported criteria for defining and detecting AKI is an abrupt (typically within about 2-7 Days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI.

For example, relationships between elevated serum creatinine and AKI has been reported to be associated with health risks. Praught et al., *Curr Opin Nephrol Hypertens* 14:265-270 (2005); and Chertow et al., *J Am Soc Nephrol* 16:3365-3370 (2005) (both references are herein incorporated by reference in their entirety). As described in these publications, acute worsening renal function (AKI) and increased risk of death and other detrimental outcomes are now known to be associated with very small increases in serum creatinine. These creatinine increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 Days, 3 Days, 7 Days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

Another study correlated serum creatinine levels with post-surgical mortality rates. Following heart surgery, patients with a mild fall in serum creatinine (i.e., for example, between approximately −0.1 to −0.3 mg/dL) had the lowest mortality rate, wherein patients had a larger mortality rate associated with either large falls in serum creatinine (i.e., for example, more than or equal to −0.4 mg/dL), or an increase in serum creatinine. Lassnigg et al., *J Am Soc Nephrol* 15:1597-1605 (2004), herein incorporated by reference in its entirety. These findings suggested that even very subtle changes in renal function, as detected by small creatinine changes within 48 hours of surgery, can be predictive of a patient's outcome.

A unified classification system using serum creatinine to define AKI in clinical trials and in clinical practice was proposed to stratify AKI patients. Bellomo et al., *Crit. Care* 8(4):R204-212 (2004), which is herein incorporated by reference in its entirety. For example, a serum creatinine rise of 25% may define contrast-induced nephropathy. McCollough et al, *Rev Cardiovasc Med.* 7(4):177-197 (2006), herein incorporated by reference in its entirety. Although various groups propose slightly different criteria for using serum creatinine to detect AKI, the consensus is that small changes in serum creatinine, such as 0.3 mg/dL (i.e., for example, approximately 25%) are sufficient to detect AKI that characterizes a worsening renal function and that the magnitude of the serum creatinine change may be an indicator of the severity of the AKI and mortality risk.

Although serial measurement of serum creatinine over a period of Days is an accepted method of detecting and diagnosing AKI patients, serum creatinine is generally regarded to have several limitations in the diagnosis, assessment and monitoring of AKI patients. The time period for serum creatinine to rise to approximately 0.3 mg/dL (25%) is considered diagnostic for AKI can be 48 hours or longer depending on the definition used.

Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Until defined by some embodiments of the present invention, there were no methods to determine whether some patients with AKI would recover fully, or whether some would need dialysis (either short term or long term), or whether some would have other detrimental outcomes including, but not limited to, death, major adverse cardiac events or chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

B. Chronic Kidney Failure

Unlike acute renal failure, chronic renal failure slowly gets worse. It most often results from any disease that causes gradual loss of kidney function. It can range from mild dysfunction to severe kidney failure. Chronic renal failure may lead to end-stage renal disease (ESRD).

Chronic renal failure usually occurs over a number of years as the internal structures of the kidney are slowly damaged. In the early stages, there may be no symptoms. In fact, progression may be so slow that symptoms do not occur until kidney function is less than one-tenth of normal.

Chronic renal failure and ESRD affect more than 2 out of 1,000 people in the United States. Diabetes and high blood pressure are the two most common causes and account for most cases. Other major causes include, but are not limited to, Alport syndrome, analgesic nephropathy, glomerulonephritis of any type (one of the most common causes), kidney stones and infection, obstructive uropathy, polycystic kidney disease, or reflux nephropathy. Chronic renal failure results in an accumulation of fluid and waste products in the body, leading to a build up of nitrogen waste products in the blood (azotemia) and general ill health. Most body systems are affected by chronic renal failure.

Initial symptoms may include, but are not limited to, fatigue, frequent hiccups, general ill feeling, generalized itching (pruritus), headache, nausea, vomiting, or unintentional weight loss. Further, later symptoms may include, but are not limited to, blood in the vomit or in stools, decreased alertness, including drowsiness, confusion, delirium, orcoma, decreased sensation in the hands, feet, or other areas, easy bruising or bleeding, increased or decreased urine output, muscle twitching or cramps, seizures, or white crystals in and on the skin (uremic frost).

Circulating levels of cytokines and other inflammation markers are markedly elevated in patients with chronic renal failure. This could be caused by increased generation, decreased removal, or both. However, it is not well established to what extent renal function per se contributes to the uremic proinflammatory milieu. Relationships between inflammation and glomerular filtration rate (GFR) were reported in 176 patients (age, 52+/−1 years; GFR, 6.5+/−0.1 mL/min) close to the initiation of renal replacement therapy. Pecoits-Filho et al., "Associations between circulating inflammatory markers and residual renal function in CRF patients" *Am J Kidney Dis.* 41(6):1212-1218 (2003). For example, circulating levels of high-sensitivity C-reactive protein (hsCRP), tumor necrosis factor-alpha (TNF-alpha), interleukin-6 (IL-6), hyaluronan, and neopterin were measured after an overnight fast. Patients subsequently were subdivided into two groups according to median GFR (6.5 mL/min). Despite the narrow range of GFR (1.8 to 16.5 mL/min), hsCRP, hyaluronan, and neopterin levels were significantly greater in the subgroup with lower GFRs, and significant negative correlations were noted between GFR and IL-6 (rho=−0.18; P<0.05), hyaluronan (rho=−0.25; P<0.001), and neopterin (rho=−0.32; P<0.0005). In a multivariate analysis, age and GFR were associated with inflammation but cardiovascular disease and diabetes mellitus were not. These results show that a low GFR per se is associated with an inflammatory state, suggesting impaired renal elimination of proinflammatory cytokines, increased generation of cytokines in uremia, or an adverse effect of inflammation on renal function.

C. Dialysis

Dialysis (i.e., for example, renal replacement therapy) is a method of removing toxic substances (impurities or wastes) from the blood when the kidneys are unable to do so and can be performed using several different methods. For example, peritoneal dialysis may filter waste by using the peritoneal membrane inside the abdomen. The abdomen is filled with special solutions that help remove toxins. The solutions remain in the abdomen for a time and then are drained out. This form of dialysis can be performed at home, but must be done every Day. Alternatively, hemodialysis may be performed by circulating the blood through special filters outside the body. The blood flows across a filter, along with solutions that help remove toxins.

Dialysis uses special ways of accessing the blood in the blood vessels. The access can be temporary or permanent. Temporary access takes the form of dialysis catheters—hollow tubes placed in large veins that can support acceptable blood flows. Most catheters are used in emergency situations for short periods of time. However, catheters called tunneled catheters can be used for prolonged periods of time, often weeks to months. Permanent access is created by surgically joining an artery to a vein. This allows the vein to receive blood at high pressure, leading to a thickening of the vein's wall. This vein can handle repeated puncture and also provides excellent blood flow rates. The connection between an artery and a vein can be made using blood vessels (an arteriovenous fistula, or AVF) or a synthetic bridge (arteriovenous graft, or AVG). Blood is diverted from the access point in the body to a dialysis machine. Here, the blood flows counter-current to a special solution called the dialysate. The chemical imbalances and impurities of the blood are corrected and the blood is then returned to the body. Typically, most patients undergo hemodialysis for three sessions every week. Each session lasts 3-4 hours. The purpose of dialysis is to assist kidney functions including, filters for the blood, removing waste products, regulating body water, maintaining electrolyte balance, or maintaining blood pH remains between 7.35 and 7.45. Further, dialysis may replace some of the functions for kidneys that aren't working properly that would otherwise result in the death of a patient.

Dialysis is most often used for patients who have kidney failure, but it can also quickly remove drugs or poisons in acute situations. This technique can be life saving in people with acute or chronic kidney failure.

II. Urinary Renal Biomarkers

Currently, no effective treatments exist to improve renal recovery, or to improve short and long-term renal outcome, after AKI. Furthermore, methods to predict recovery are also lacking. The emerging role of biomarkers for early detection of renal disease and/or renal injury may help identify new prognostic tools to predict renal clinical outcomes. Potential candidates for biomarkers of renal recovery include, but are not limited to, molecules expressed in pathways leading to regeneration and proliferation as well as markers of fibrosis and apoptosis. In addition, renal injury biomarkers may also serve to distinguish early resolution, and hence increased odds of recovery.

Acute kidney injury (AKI) has an estimated incidence rate of approximately 2000 per million population and this rate is increasing. Ali et al., "Incidence and outcomes in acute kidney injury: a comprehensive population-based study" *J Am Soc Nephrol* 18:1292-1298 (2007). Approximately 5% of all people admitted to intensive care units around the world develop severe AKI requiring dialysis. Uchino et al., "Acute renal failure in critically ill patients: a multinational, multicenter study" *JAMA* 294:813-818 (2005). A recent, United States multicenter study found that fewer than only about 60% patients surviving severe AKI recovered renal function by two months. Palevsky et al., "Intensity of renal support in critically ill patients with acute kidney injury" *N Engl J Med* 359:7-20 (2008). Thus, a large number of patients with AKI progress into end-stage renal disease (ESRD).

However, since only a fraction of patients with AKI fail to recover renal function, interventions aimed at improving recovery or at providing renal support (e.g. early dialysis) cannot be selectively targeted appropriately without some means of determining which patients will recover and which will not recover (i.e., for example, the availability of non-invasive biomarkers). Currently, clinical risk prediction for recovery after AKI is extremely limited. Thus, development of a non-invasive biomarker that allows early prediction of recovery of kidney function is a long felt need in the art of renal disease management.

The identification of such non-invasive biomarkers (i.e., for example, a urinary biomarker) would greatly improve long-term prognosis thereby tailoring research efforts to treat AKI and prevent ESRD. In other words, having the ability to predict which patients will not recover kidney function allows a clinician to focus limited resources on the development and application of aggressive treatment interventions on these predicted at-risk patients. Conversely, patients with a favorable prognosis would be spared from more aggressive interventions and their potential adverse effects, thereby releasing medical resources to those in need and reducing overall medical costs.

In one embodiment, the present invention contemplates methods and compositions for evaluating renal function in a subject. As described herein, measurement of various kidney injury markers described herein can be used for diagnosis, prognosis, risk stratification, staging, monitoring, categorizing and a determination of further diagnosis and treatment regimens in subjects suffering or at risk of suffering from an injury to renal function, reduced renal function, and/or acute renal failure (also called acute kidney injury).

Renal biomarkers as described herein may be used individually, or in panels, comprising a plurality of renal biomarkers, for risk stratification. In one embodiment, risk stratification identifies subjects at risk for a future: i) injury to renal function; ii) progression to reduced renal function; iii) progression to ARF; or iv) improvement in renal function, etc. In one embodiment, risk stratification diagnoses an existing disease, comprising identifying subjects who have: i) suffered an injury to renal function; ii) progressed to reduced renal function; or iii) progressed to ARF, etc. In one embodiment, risk stratification monitors for deterioration and/or improvement of renal function. In one embodiment, risk stratification predicts a future medical outcome including, but not limited to, an improved or worsening renal function, a decreased or increased mortality risk, a decreased or increased risk that a subject will require initiation or continuation of renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In one embodiment, the present invention contemplates methods for evaluating renal status in a subject. In one embodiment, the method provides a body fluid sample derived from the subject. In one embodiment, the method comprises performing an assay using the body fluid sample for detecting one or more renal biomarkers selected from the group including, but not limited to, hyaluronic acid (HA), death receptor 5 (DR5), or transforming growth factor β1 (TGFβ1). The assay measurement, for example, a measured concentration of HA, DR5, and/or TGFβ1, is/are then correlated to with a threshold value to establish the renal status of the subject.

Correlations to establish a patient's renal status may include, but is not limited to, correlating the assay measurement to one or more of risk stratification, diagnosis, prognosis, staging, classifying and monitoring of the subject as described herein. Thus, the present invention utilizes one or more renal biomarkers of the present invention for the evaluation of renal disease and/or injury.

A variety of methods may be used to arrive at a desired threshold value for use in these methods. For example, a threshold value may be determined from a population of normal subjects by selecting a renal biomarker concentration representing the 75th, 85th, 90th, 95th, or 99th percentile of the biomarker as measured in such normal subjects. Alternatively, a threshold value may be determined from a "diseased" population of subjects, e.g., those suffering from an injury or having a predisposition for an injury (e.g., progression to ARF or some other clinical outcome such as death, dialysis, renal transplantation, etc.), by selecting a renal biomarker concentration representing the 75th, 85th, 90th, 95th, or 99th percentile of the biomarker as measured in such diseased subjects. In another alternative, the threshold value may be determined from a prior measurement of a renal biomarker in the same subject; that is, a temporal change in the level of the biomarker in the subject may be used to assign risk to the subject.

The foregoing discussion is not meant to imply, however, that renal biomarkers contemplated herein are limited to a comparison to corresponding individual thresholds. Other methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual biomarkers may be treated as if it is itself a biomarker; that is, a threshold value may be determined for the composite result as described herein for individual biomarkers, and the composite result for an individual patient compared to this threshold value.

In one embodiment, the present invention contemplates a urinary hyaluronic acid (HA) biomarker to predict recovery of renal function after renal injury and/or disease. In one embodiment, identifying the biomarker provides patient stratification to tailor treatment intensity thereby preventing unnecessary long-term complications.

In one embodiment, the present invention contemplates a method comprising predicting long-term prognosis of a renal injury and/or disease early after onset the renal injury and/or disease. In one embodiment, the method predicts long-term dialysis when urinary HA is persistently elevated between D1-D14 after initiation of replacement therapy for severe acute kidney injury. In one embodiment, the method predicts long-term dialysis when urinary HA is persistently elevated between D1-D14 after initiation of replacement therapy for severe acute kidney injury. In one embodiment, the long-term dialysis comprises at least sixty (60) Days after kidney injury. In one embodiment, the long-term dialysis comprises at least sixty (60) Days after kidney disease diagnosis.

Some data provided herein was collected from forty-three (43) patients enrolled in a large multicenter randomized controlled trial studying the effect of different RRT doses on AKI survival. In one embodiment, AKI survival was correlated with a urinary hyaluronic acid (HA) biomarker. Although it is not necessary to understand the mechanism of an invention, it is believed that HA (i.e., for example, hyaluronan or hyaluronate) comprises a non-sulfated glycosaminoglycan, and is believed widely distributed throughout connective, epithelial, and neural tissues. HA is also believed to be one of several components within the extracellular matrix and may be involved in tissue repair and remodeling by mediating cell proliferation and migration, synthesis and degradation of extracellular matrix. For example, fragmented HA has been observed to accumulate during tissue injury and may stimulate the expression of inflammatory genes by a variety of immune cells at the injury site. Further, impaired clearance of HA has been seen to result in persistent inflammation.

Figure 5:
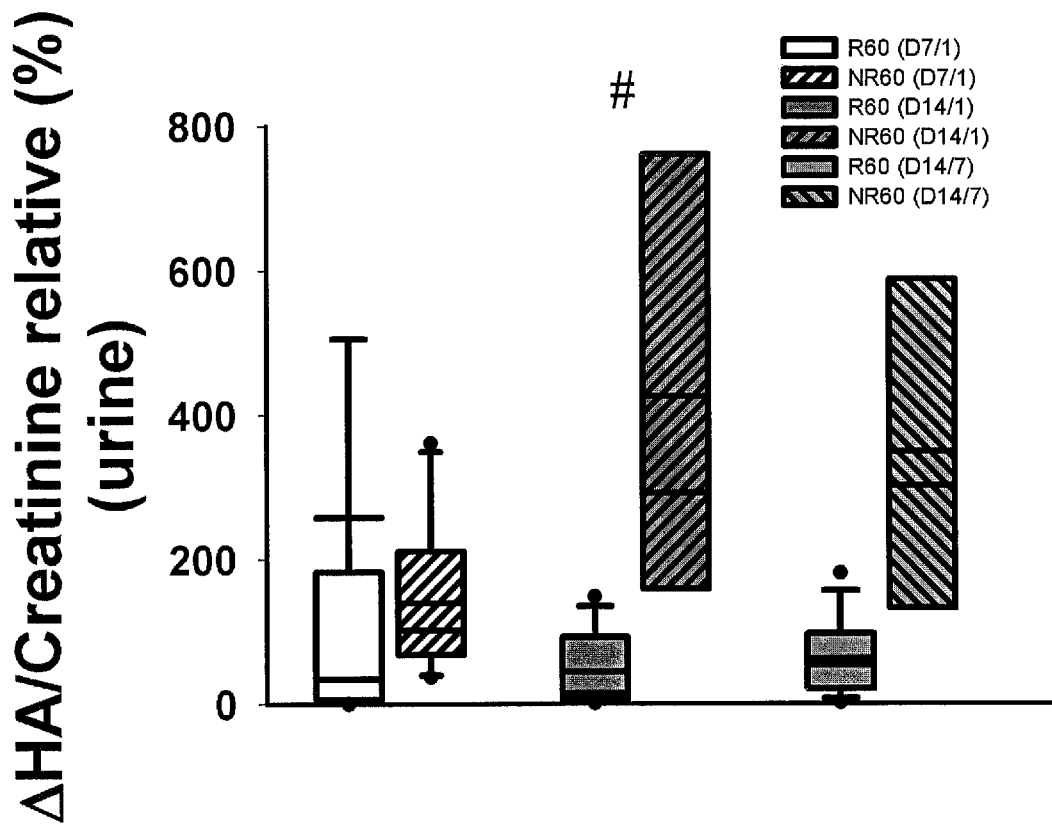
FIG. 5 presents exemplary data showing relative differences between urine samples taken on D1, D7 and/or D14 from patients either recovering or not recovering sixty Days after kidney injury (R60 and NR60, respectively).

In one embodiment, the biomarker predicts a non-recovery of renal function, wherein dialysis-dependence is in excess of sixty (60) Days. In one embodiment, non-recovery of renal function comprises biomarker elevation above its initial value for at least fourteen (14) Days. In one embodiment, the biomarker prediction is supported by a receiver operating characteristic (ROC) analysis. In one embodiment, the ROC analysis provides calculations including, but not limited to, area under fitted curve and/or trapezoidal (Wilcoxon) area. In one embodiment, the area under fitted curve=0.9686 having an estimated standard error=0.0518. In one embodiment, the trapezoidal (Wilcoxon) area=0.9692 having an estimated standard error=0.0568). See, FIG. 5.

A. Hyaluronic Acid

Hyaluronic acid (HA) is believed to be a ubiquitous connective tissue glycosaminoglycan that in vivo is present as a high molecular mass component of most extracellular matrices. HA has not been identified as a major constituent of the normal renal corticointerstitium. Hansell et al., "Hyaluronan content in the kidney in different states of body hydration" *Kidney Int* 58:2061-2068 (2000). Nonetheless, HA is expressed around renal proximal tubular epithelial cells (PTC) after both acute and chronic renal injury that is caused by numerous diseases. Sibalic et al., "Upregulated renal tubular CD44, hyaluronan, and osteopontin in kdkd mice with interstitial nephritis" *Nephrol Dial Transplant* 12:1344-1353 (1997); and Lewington et al., "Expression of CD44 in kidney after acute ischemic injury in rats" *Am J Physiol Regul Integr Comp Physiol* 278:R247-254 (2000). Furthermore, increased deposition of interstitial HA correlates with both proteinuria and renal function in progressive renal disease. Sano et al., "Localization and roles of CD44, hyaluronic acid and osteopontin in IgA nephropathy" *Nephron* 89:416-421 (2001).

Binding of HA to its principle receptor, CD44, promotes inflammation through interaction between HA and CD44, expressed on inflammatory cells. Melin et al., "Ischemia-induced renal expression of hyaluronan and CD44 in diabetic rats" *Nephron Exp Nephrol* 103:e86-94 (2006). HA/CD44 binding activates the mitogen-activated protein kinase (MAPK) pathway and enhances PTC migration, a process that is implicated in epithelial cell-fibroblast trans-differentiation and progressive renal fibrosis. Yang et al., "Dissection of key events in tubular epithelial to myofibroblast transition and its implications in renal interstitial fibrosis" *Am J Pathol* 159:1465-1475 (2001). In ischemic kidneys from diabetic subjects, the renal HA content started to increases already after 24 hours and significantly so 1-8 weeks after ischemia/reperfusion (I/R). Okajima K: "Regulation of inflammatory responses by natural anticoagulants" *Immunol Rev* 184:258-274 (2001).

Hyaluronic acid (also known in the art as hyaluronate and hyaluronan, and abbreviated as HA), is a glycosaminoglycan comprising a straight unbranched polysaccharide chain with alternating units of N-acetyl-D-glucosamine and D-glucuronic acid. Laurent et al., "Hyaluronan" *FASEB J* 6:2397-2404 (1992); and Delpech et al., "Hyaluronan: fundamental principles and applications in cancer" *J Intern Med* 242: 41-48 (1997). HA is present ubiquitously in various types of biological material, including both bacteria and animals. In humans, HA is found in high concentrations in umbilical cords, vitreous humor of the eyes, cartilage and synovial fluid. Small amounts of HA are present in CSF, lymph, blood, serum and urine. Levels of HA have been associated with diseases such as rheumatoid arthritis, liver cirrhosis, and Wilms' tumor. HA is associated with non-specific tumors in general, but its use has not been applied heretofore to the discovery, therapy and management of particular clinical tumors. HA has been known to play a role in several pathophysiological conditions including cancer.

For example, HA levels have been shown to be elevated in certain animal tumor models (e.g., rabbit V2 carcinoma) and human cancers (e.g., lung, Wilms' tumor, breast, etc.). Knudson et al., "The role and regulation of tumor associated hyaluronan" In: The Biology of Hyaluronan (J. Whelan, ed.), pp. 150-169, New York, Wiley Chichister (Ciba Foundation Symposium 143), 1989). In tumor tissues, HA supports tumor cell adhesion and migration and also offers some protection against immune surveillance.

Small fragments of HA has also been observed to stimulate angiogenesis, and such fragments are found in the urine of bladder carcinoma patients and tumor tissues. Sattar et al., "Does hyaluronan have a role in endothelial cell proliferation of the synovium?" *Semin Arthritis Rheum* 22:37-43 (1992); Lokeshwar V B, Selzer M G. Differences in hyaluronic acid mediated functions and signaling in arterial, microvessel, and vein-derived human endothelial cells. J Biol Chem 2000; 275:27641-27649. Hyaluronic acid fragments are generated when HAase, an endoglycosidase, degrades the HA polymer. Csoka T B, Frost G I, Stern R. Hyaluronidases in tissue invasion. Invasion Metastasis 1997; 17:297-311; and 55. Roden L, Campbell P, Fraser J R, Laurent T C, Petroff H, Thompson J N. Enzymatic pathways of hyaluronan catabolism. In: Whelan J, editor. The Biology of Hyaluronan. New York: Wiley Chichister 1989:60-86. A HA test has been suggested to detect bladder carcinoma, regardless of the tumor grade. Lokeshwar V B, Obek C, Pham H T, Wei D, Young M J, Duncan R C. Urinary hyaluronic acid and hyaluronidase: markers for bladder cancer detection and evaluation of grade. J Urol 2000; 163:348-356.

The efficacy of the HA-HAase test to monitor bladder tumor recurrence as compared to the standard BTA-Stat was recently reported. Lokeshwar et al., Bladder Tumor Markers for Monitoring Recurrence and Screening Comparison of Hyaluronic Acid-Hyaluronidase and BTA-Stat Tests Cancer 95:61-72 (2002). This study suggested that a biochemical test such as the HA-HAase test can detect bladder carcinoma recurrence earlier than cystoscopy. If such early detection can provide a clinical advantage in terms of outcome, cystoscopy may not remain the ultimate gold standard to decide a test's sensitivity, specificity, and accuracy in monitoring recurrence. An interesting corollary to this would be treatment of prostate carcinoma patients and increasing prostate specific antigen after radical prostectomy or radiation therapy the HA-HAase test can be an effective adjunct to cystoscopy for monitoring bladder carcinoma recurrence. With over 90% sensitivity and 86% accuracy, the HA-HAase test can be an effective adjunct to cystoscopy for monitoring bladder carcinoma recurrence. A false-positive HA-HAase test carries a significant risk of recurrence within five months. Thus, it is possible that a combination of biochemical tests can effectively monitor bladder carcinoma recurrence, which may allow a minimum 50% reduction in the number of surveillance cystoscopy procedures.

Hyaluronidase (HAase) is an endoglycosidic enzyme that degrades HA by hydrolyzing the N-acetylglucosaminic bonds in HA. The limited degradation of HA by hyaluronidase results in the generation of HA fragments of specific lengths (~3-25 disaccharide units) that are angiogenic (West et al., Angiogenesis induced by degradation products of hyaluronic acid. Science, 228: 1324-1326, 1985). In vertebrates, hyaluronidases can be categorized into two classes, those active at neutral pH (pH optimum 5.0), and those active at acidic pH (pH 3.5-4.0) (Roden et al., Enzymatic pathways of hyaluronan catabolism. In: The Biology of hyaluronan, (J. Whelan, ed.), pp. 60-86, New York, Wiley Chichister (Ciba Foundation Symposium 143), 1989; West et al., ibid.; Gold, Purification and properties of hyaluronidase from human liver. Biochem. J., 205: 69-74, 1982; Fraser and Laurent, Turnover and metabolism of Hyaluronan. in: Biology of Hyaluronan, (J. Whelan, ed.), pp. 41-59, New York, Wiley Chichister (Ciba Foundation Symposium 143), 1989; Zhu et al., Molecular cloning of a mammalian hyaluronidase reveals identity with hemopexin, a serum heme-binding protein. J. Biol. Chem., 269: 32092-32097, 1994; Lin et al., A hyaluronidase activity of the sperm plasma membrane protein PH-20 enables sperm to penetrate the cumulus layer surrounding the egg. J. Cell Biol., 125: 1157-1163, 1995). For example, the testicular hyaluronidase is of neutral type whereas the liver hyaluronidase has an acidic pH optimum. The concerted actions of both HA and hyaluronidases are known to play important roles during embryonic development, vasculogenesis, vascular remodeling, immune surveillance and tumor progression (McCormick and Zetter, Adhesive interactions in angiogenesis and metastasis. Pharmacol. Ther., 53: 239-260, 1992; Hobarth et al., Topical chemo-prophylaxis of superficial bladder cancer by mitomycin C and adjuvant hyaluronidase, Eur. Urol., 21: 206-210, 1992; Knudson et al., The role and regulation of tumor-associated hyaluronan. In: The Biology of Hyaluronan (J. Whelan, ed.) pp. 150-169, New York, Wiley, Chichester (Ciba Foundation Symposium 143), 1989; Lin et al., Urinary hyaluronic acid is a Wilms' tumor marker. J. Ped. Surg., 30: 304-308, 1995; Stern et al., Hyaluronidase levels in urine from Wilms' tumor patients. J. Natl. Canc. Inst., 83: 1569-1574, 1991).

B. Death Receptor 5

Death receptor 5 (DR5) believed to be a pro-apoptotic receptor that is activated by tumor necrosis factor-related apoptosis-inducing ligand (TRAIL). TRAIL is believed to be a soluble form of an endogenous apoptosis-inducing ligand inducing apoptosis in a broad range of cells and contributing subsequent inflammation and fibrosis. TRAIL or DR5 deficient mice have been reported to be relatively resistant to occurrence of inflammation and subsequent fibrosis. Wang et al., "Over-expression of C/EBP-alpha induces apoptosis in cultured rat hepatic stellate cells depending on p53 and peroxisome proliferator-activated receptor-gamma" Biochem Biophys Res Commun 380:286-291 (2009); and Takeda et al., "Death receptor 5 mediated-apoptosis contributes to cholestatic liver disease" Proc Natl Acad Sci USA 105:10895-10900 (2008).

The data presented herein exemplifies a screening method for a series of urinary proteins that are relevant to inflammation, sepsis, acute kidney injury, and acute renal failure. From this panel, urinary Death Receptor 5 (DR5) was identified as a potential biomarker of recovery after severe AKI. Death Receptor 5 (also known as TRAILR2) is part of the Tumor Necrosis Factor (TNF) Superfamily, and is a receptor for Tumor Necrosis Factor-Related Apoptosis Inducing Ligand (TRAIL). Upon the binding of TRAIL to its receptors (DR4 and DR5) a cascade of events is initiated leading to NFkB activation and apoptosis. Shetty et al., "Tumor necrosis factor-related apoptosis inducing ligand (TRAIL) up-regulates death receptor 5 (DR5) mediated by NFkB activation in epithelial cell lines" Apoptosis 7:413-420 (2002).

In one embodiment, the present invention contemplates a urinary biomarker comprising DR5 capable of predicting post-AKI renal function recovery. In one embodiment, the present invention contemplastes a urinary biomarker comprising DR5 capable of providing a patient stratification for post-AKI treatment intensity and prevention of long-term complications.

C. Transforming Growth Factor β1

Transforming growth factor-β1 (TGFβ1) is believed to be a secreted protein that performs many cellular functions, including but not limited to proliferation, differentiation and apoptosis. TGFβ1 may act directly by stimulating synthesis of extracellular matrix components and reducing collagenase production, or indirectly through other profibrogenic factors such as connective tissue growth factor (CTGF) which may play a role in glomerulosclerosis, interstitial fibrosis and tubular atrophy occurring with end-stage kidney failure, irrespective of the primary etiology. Wolf G., "Renal injury due to renin-angiotensin-aldosterone system activation of the transforming growth factor-beta pathway" Kidney Int 70:1914-1919 (2006). TGFβ1 is also highly expressed following ischemia/reperfusion (I/R) and promotes blood vessel loss by inducing phenotypic transition of endothelial cells to transdifferentiate into a fibroblast/myofibroblasts phenotype.

The data presented herein screens a series of urinary proteins related to renal physiology. From this panel, urinary Transforming Growth Factor β1 (TGF-β1) was identified as potential biomarker of renal recovery after severe AKI. TGF-β1 is growth factor involved in embryological development and in tissue healing and repair. TGF-β1 is known to be involved in renal tubular epithelial cell signaling. Sakurai et al., "An in vitro tubulogenesis system using cell lines derived from the embryonic kidney shows dependence on multiple soluble growth factors" Proc Natl Acad Sci USA 94:6279-6284 (1997).

In one embodiment, the present invention contemplates a urinary biomarker comprising TGF-β1 capable of predicting post-AKI renal function recovery. In one embodiment, the present invention contemplastes a urinary biomarker comprising TGF-β1 capable of providing a patient stratification for post-AKI treatment intensity and prevention of long-term complications.

D. Clinical Trial Results

1. Experimental Design

A recent kidney recovery study (BioMARK) was an observational cohort study conducted as a part of the Veterans Affairs/National Institutes of Health (VA/NIH) Acute Renal Failure Trial Network study (hereinafter referred to as the ATN study). The ATN study comprised a multicenter, prospective trial of two strategies for renal-replacement therapy in critically ill patients with acute kidney injury. The ATN study was conducted between November 2003 and July 2007 at 27 Veterans Administration and university-affiliated medical centers. All adult patients (18 years or older) had AKI clinically consistent with acute tubular necrosis (defined as a clinical setting of ischemic or nephrotoxic injury and oliguria or increased serum creatinine) and requiring renal-replacement therapy (RRT), as well as failure of one or more non-renal organ systems or sepsis.

Exclusion criteria included: i) baseline serum creatinine more than 2 mg/dl in males or more than 1.5 mg/dl in females; ii) AKI clinically believed to be due to an etiology other than acute tubular necrosis; iii) prior kidney transplantation; iv) pregnancy; v) incarceration; vi) weight more than 120 kg; vii) non-candidacy for RRT; viii) moribund state; or ix) patient not expected to survive 28-Day because of an irreversible medical condition. Eligible patients could not have undergone more than one session of intermittent hemodialysis or sustained low-efficiency dialysis or more than 24 hours of continuous renal-replacement therapy before randomization.

As a sub-study of the ATN trial, some patients enrolled at University of Pittsburgh Medical Center, Pittsburgh VA Medical Center, Cleveland Clinical Foundation, University of Texas Health Science Center at Houston, and Washington University Medical Center were asked to undergo serial measurements of selected prospective biomarkers (i.e., for example, hyaluronic acid, transforming growth factor β1, or death receptor 5). This particular study required an additional consent form for biomarker determination, and a total of 76 cases from these 5 centers were available for analysis and included into the study. Approval was obtained from the Institutional Review Boards of the University of Pittsburgh and all participating sites.

2. Data Collection and Analysis

Medical records of study participants were prospectively reviewed to retrieve hospitalization data, including baseline demographic characteristics, serial renal function, and/or the presence of oliguria (as defined by urine output <400 ml/Day). The presence of sepsis was defined by using the systemic inflammatory response syndrome criteria. Definition of renal recovery was modified from the $2^{nd}$ International Consensus Conference of the acute dialysis quality initiative (ADQI) group. Recovery of renal function was defined by long-term survival or dialysis independence. Non-recovery was defined by non-survival or dialysis independence.

Fresh urinary samples were obtained at the following times: Day 1, Day 7, and Day 14 after enrollment. After centrifuging the urine for 5 minutes at 1000×g at 4° C., urine samples were aliquotted and stored at −80° C. No samples were thawed and refrozen before study. Urine creatinine concentrations were measured using a commercially available enzymatic assay (DZ072B, Diazyme labs, California, USA); urinary HA was measured using a commercially available assay (Echelon Biosciences, Salt Lake City, USA); and TGFβ1 was measured using a commercially available assay (R&D, Minneapolis, USA). All were measured according to the respective manufacturer's instructions. DR5 was measured by a chemiluminescent immunoassay using an automated analyzer (IMMULITE®; Diagnostic Products Corp, Los Angeles, Calif.).

The outcome of recovery as dialysis independence was defined as occurring on Day 60. Baseline characteristics were compared between patients who recovered from AKI by 60 Day after enrollment and those who failed to recover. Continuous data were expressed as mean±SD and compared using the student's t test or Wilcoxon rank-sum test. Categorical data were expressed as proportions and compared using the chi-squared test or Fisher's exact test. The renal biomarker levels were normalized by urine creatinine concentrations and analyzed at each time point. An analysis was then performed using the largest relative change within the first 14 Days as compared to Day 1 and the last available measurement for each patient. A logistic regression was then fitted to the dataset to evaluate the association between each potential biomarker and recovery of AKI. Consequently, the area under the receiver-operating characteristic curve (AUC ROC) was generated to assess the prediction accuracy of each renal biomarker. The optimal cut-off points were determined by the largest sum of sensitivity and specificity. To assess the additive prediction ability of each renal biomarker to the traditional clinical predictors, a clinical prediction model was identified based on the AUC ROC analysis and then added each renal biomarker individually to this clinical model. The AUC ROCs from the combined models were compared with the AUC ROCs of the clinical model. All the analyses were performed using SAS 9.0 (SAS Institute, Cary, N.C.) at a significance level of 0.05.

3. Results

Clinical characteristics of the 76 patients are summarized in Table 2.

TABLE 2

| Demographic And Clinical Indicia | | | | |
|---|---|---|---|---|
| Characteristic | All subjects (n = 76) | Non Recovery (n = 38) | Recovery (n = 38) | P value |
| Age | 58.42 ± 17.03 | 64.66 ± 16.20 | 52.18 ± 15.68 | <0.001 |
| Gender: Female (%) | 30 (39.47) | 15 (39.47) | 15 (39.47) | 1.000 |
| Race: White (%) | 64 (84.21) | 34 (89.47) | 30 (78.95) | 0.208 |
| Cause of AKI | | | | |
| Ischemia (%) | 66 (86.84) | 37 (97.37) | 29 (76.32) | 0.007 |
| Nephrotoxicity (%) | 16 (21.33) | 6 (16.22) | 10 (26.32) | 0.286 |
| Sepsis (%) | 50 (65.79) | 27 (71.05) | 23 (60.53) | 0.334 |
| Multifactor (%) | 51 (68) | 26 (70.27) | 25 (65.79) | 0.678 |
| Baseline creatinine | 1.13 ± 0.44 | 1.18 ± 0.46 | 1.08 ± 0.43 | 0.446 |
| Baseline BUN | 55.59 ± 29.94 | 59.87 ± 30.82 | 51.32 ± 28.80 | 0.234 |
| Treatment group: intensive (%) | 34 (44.74) | 16 (42.11) | 18 (47.37) | 0.645 |
| Length of ICU stay before randomization | 5.38 ± 4.12 | 6.53 ± 4.90 | 4.24 ± 2.79 | 0.033 |
| Mechanical ventilation (%) | 69 (90.79) | 35 (92.11) | 34 (89.47) | 0.500 |
| Length of hospital stay before randomization | 8.47 ± 7.14 | 10.24 ± 8.48 | 6.71 ± 5.00 | 0.083 |
| Charlson comorbidity index | 4.09 ± 3.34 | 4.88 ± 2.69 | 3.34 ± 3.75 | 0.008 |
| APACHE II score | 23.35 ± 7.15 | 24.97 ± 6.78 | 21.77 ± 7.24 | 0.062 |
| Non renal SOFA score - respiratory on Day 1 | 2.50 ± 1.07 | 2.63 ± 1.19 | 2.38 ± 0.95 | 0.296 |
| Non renal SOFA score - coagulation on Day 1 | 1.59 ± 1.28 | 1.58 ± 1.32 | 1.61 ± 1.25 | 0.926 |
| Non renal SOFA score - liver on Day 1 | 1.63 ± 1.41 | 2.10 ± 1.45 | 1.11 ± 1.20 | 0.030 |
| Non renal SOFA score - cardiovascular on Day 1 | 2.24 ± 1.68 | 2.50 ± 1.64 | 1.97 ± 1.70 | 0.173 |

TABLE 2-continued

Demographic And Clinical Indicia

| Characteristic | All subjects (n = 76) | Non Recovery (n = 38) | Recovery (n = 38) | P value |
|---|---|---|---|---|
| Non renal SOFA score - central nerve system on Day 1 | 2.21 ± 1.39 | 2.08 ± 1.50 | 2.34 ± 1.28 | 0.454 |
| Total Day 1 SOFA score | 10.91 ± 3.40 | 11.94 ± 3.81 | 9.75 ± 2.49 | 0.035 |
| Day 1 Cleveland clinic ICU ARF Renal Failure score | 11.91 ± 2.96 | 12.21 ± 2.97 | 11.61 ± 2.97 | 0.490 | a. Day 1 Summary

There were equal numbers of patients in recovery and non-recovery group. No significant differences were found between recovery and non-recovery groups in terms of gender, race, baseline renal function, or Day 1 clinical evaluation scores (i.e., for example, APACHE II scores and/or Cleveland Clinic ICU ARF Renal Failure scores). The mean age, length of ICU stay before randomization, Charlson comorbidity index, total SOFA score on Day 1 were all significantly higher in the non-recovery group when compared to the recovery group. Ischemia was observed to have the highest percentage (97.4%) for AKI causation in the non-recovery group as compared to 76.3% in recovery group. Sepsis also was seen to be responsible for AKI more often in the non-recovery group than in the recovery group (71.05% vs. 60.53%, respectively).

b. Day 60 Recovery Prediction

Five (5) different models of individual biomarkers combinations were screened for the best area under the ROC curve (AUC ROC) for predicting recovery by Day 60. See, Table 3.

TABLE 3

Urinary Biomarker Model Correlations Predicting Recovery By Day 60

| Urinary Biomarkers | | AUC ROC (95% CI) | P value |
|---|---|---|---|
| HA | Day 1 | 0.59 (0.46, 0.73) | 0.164 |
| | Day 7 | 0.44 (0.28, 0.59) | 0.422 |
| | Day 14 | 0.89 (0.75, 1.00) | <0.001 |
| | Largest relative change | 0.78 (0.65, 0.90) | <0.001 |
| | Last available Day | 0.30 (0.18, 0.42) | 0.001 |
| DR5 | Day 1 | 0.56 (0.43, 0.69) | 0.381 |
| | Day 7 | 0.64 (0.48, 0.80) | 0.083 |
| | Day 14 | 0.68 (0.51, 0.82) | 0.088 |
| | Largest relative change | 0.67 (0.47, 0.90) | 0.032 |
| | Last available Day | 0.70 (0.58, 0.83) | 0.001 |
| TGFβ1 | Day 1 | 0.61 (0.48, 0.74) | 0.089 |
| | Day 7 | 0.52 (0.35, 0.68) | 0.848 |
| | Day 14 | 0.70 (0.48, 0.91) | 0.074 |
| | Largest relative change | 0.68 (0.53, 0.83) | 0.016 |
| | Last available Day | 0.57 (0.43, 0.70) | 0.327 |

The data demonstrate that Day 14 HA, Day 14 TGFβ1, and the last available values of DR5 were the best predictors of AKI recovery with AUC ROCs ranging from 0.70 to 0.89. The optimized clinical model was a combination of age and Charlson comorbidity index, which indicated a significant AUC ROC of 0.74 for AKI recovery. Great improvements of AUC ROCs were observed when urinary renal biomarkers were added to the clinical model. AUC ROCs of the clinical model indicies combined with relative changes of HA, DR5, and TGFβ1 were 0.83, 0.86, 0.84 and 0.91 respectively, wherein AUC ROC reaches 0.97 when Day 14 HA is combined with age (P<0.001 in all above models; Table 4).

TABLE 4

Improved Prediction Using Clinical Model Combinations

| | Markers | AUC (95% CI) | P value |
|---|---|---|---|
| Individual clinical parameters | Age | 0.73 (0.61, 0.84) | <0.001 |
| | Total SOFA score | 0.71 (0.53, 0.89) | 0.022 |
| | Charlson comorbidity index | 0.69 (0.56, 0.82) | 0.004 |
| | APACHIE II score | 0.63 (0.50, 0.76) | 0.053 |
| Clinical Model | Age* + Charlson comorbidity index | 0.74 (0.62, 0.87) | <0.001 |
| Clinical + HA | Day 1 | 0.75 (0.63, 0.87) | <0.001 |
| | Day 14 | 0.97 (0.90, 1.00) | <0.001 |
| | Largest Relative change | 0.83 (0.71, 0.95) | <0.001 |
| Clinical + DR5 | Day 1 | 0.76 (0.64, 0.88) | <0.001 |
| | Day 14 | 0.85 (0.67, 1.00) | <0.001 |
| | Largest Relative change | 0.86 (0.74, 0.97) | <0.001 |
| Clinical + TGFβ1 | Day 1 | 0.74 (0.62, 0.86) | <0.001 |
| | Day 14 | 0.83 (0.66, 1.00) | <0.001 |
| | Largest Relative change | 0.84 (0.72, 0.96) | <0.001 |

The significant time points for each urine marker were decided by choosing the maximal AUC ROC values. A clinical threshold was determined by identifying the maximal sum of sensitivity and specificity of the above five models. See, Table 3. Day 14 HA was observed to have the highest value of sensitivity 0.93 and specificity 0.83 at 12 mcg/mg·Cr. Although lower in sensitivity, the last available values of DR5, and Day 14-TGFβ1 were also determined to be predictive. See, Table 5.

TABLE 5

Urinary Biomarker Thresholds

| Markers | Significant time point* | Clinical Threshold (unit) | Sensitivity | Specificity |
|---|---|---|---|---|
| HA | Day 14 | 12 mcg/mg · Cr | 0.9286 | 0.8333 |
| DR5 | Last available Day | 2.7 ng/mg · Cr | 0.6757 | 0.7297 |
| TGFβ1 | Day 14 | 274 pg/mg · Cr | 0.6429 | 0.7500 |

No significant differences were found in regards to baseline renal function, combination of sepsis, APACHE II scores or RRT intensity between the recovery and non-recovery groups. However, patients in the non-recovery group were found to be older, more likely to have kidney ischemia, incurred longer ICU stays prior to RRT, more co-morbidities and higher SOFA scores. The data suggest that a combination of age, Day 1 total SOFA score and Charlson comorbidity index comprises a preferred clinical predictive model.

These data also demonstrate that the relative change of urinary biomarkers HA, DR5, and TGFβ1 are significantly correlated with AKI adverse outcomes. These three (3) renal biomarkers represent biological processes of ongoing renal extracellular matrix deposition, cell apoptosis, intrinsic cell phenotype transdifferentiation and tubular epithelial cell injury respectively. Although it is not necessary to understand the mechanism of an invention, it is believed that since Day 1 values represent the intensity of insults and internal cell responses, the relative change of these renal biomarkers could represent the extent of recovery regardless of individual baseline characteristics. Furthermore, a strong association between Day 14 HA with outcomes suggest that extracellular matrix deposition may play a role in the process of kidney recovery III. Renal Status Assay Measurements The ability of a particular renal biomarker assay measurement to distinguish between two populations can be established using ROC analysis. For example, ROC curves established from a "first" subpopulation (i.e., for example, a population predisposed to one or more future changes in renal status) and a "second" subpopulation (i.e., for example, a population not predisposed to one or more future changes in renal status). Calculation of these ROC curves and establising the area under these ROC curves quantitate the predictive power of the specific assay measurement. In some embodiments, predictive power established by assay measurements described herein comprise an AUC ROC greater than 0.5, preferably at least 0.6, more preferably 0.7, still more preferably at least 0.8, even more preferably at least 0.9, and most preferably at least 0.95.

A. Immunoassays

In general, immunoassays involve contacting a sample containing, or suspected of containing, a biomarker of interest with at least one antibody that specifically binds to the biomarker. A detectable signal is then generated indicative of the presence or amount of complexes formed by the binding of polypeptides in the sample to the antibody. The detectable signal is then related to the presence or amount of the biomarker in the sample. Numerous methods and devices have been reported regarding the detection and analysis of biological biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is herein incorporated by reference in its entirety, including all tables, figures and claims.

Numerous immunoassay devices and methods can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is herein incorporated by reference in its entirety, including all tables, figures and claims. Robotic instrumentation for performing these immunoassays are commercially available including, but not limited to, Beckman ACCESS®, Abbott AXSYM®, Roche ELECSYS®, Dade Behring STRATUS® systems. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in immunoassays. Solid phases that may be used to immobilize specific binding members include, but are not limited to those developed and/or used as solid phases in solid phase binding assays. Examples of suitable solid phases include, but are not limited to, membrane filters, cellulose-based papers, beads (including polymeric, latex and paramagnetic particles), glass, silicon wafers, microparticles, nanoparticles, Tenta-Gels, Agro Gels, PEGA gels, SPOCC gels, and multiple-well plates. For example, an assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

In certain embodiments, a urinary renal biomarker assay method comprises an immunoassay. For example, antibodies for use in such assays may specifically bind an epitope of a renal biomarker of interest, and may also bind one or more polypeptides that are "related" thereto, as that term is defined hereinafter. In one embodiment, the renal biomarker of interest is a fully length marker (i.e., for example, a protein). In one embodiment, the renal biomarker of interest is a protein fragment marker (i.e., for example, a peptide). Numerous immunoassay formats are available compatible with body fluid samples including, but not limited to, urine, blood, serum, saliva, tears, and plasma.

In this regard, detectable signals obtained from an immunoassay may be a direct result of complexes formed between one or more antibodies and the target biomolecule (i.e., for example, an analyte) and polypeptides containing the necessary epitope(s) to which the antibodies bind. While such assays may detect the full length biomarker and the assay result be expressed as a concentration of a biomarker of interest, the signal from the assay may actually be a result of all such "immunoreactive" polypeptides present in the sample. Expression of biomarkers may also be determined by means other than immunoassays, including protein measurements (i.e., for example, dot blots, western blots, chromatographic methods, mass spectrometry, etc.) and nucleic acid measurements (mRNA quantitation). This list is not meant to be limiting.

The foregoing method steps should not be interpreted to mean that the renal biomarker assay measurements is/are used in isolation in the methods described herein. Rather, additional variables or other clinical indicia may be included in the methods described herein. For example, risk stratification, diagnostic, classification, monitoring, etc. methods as described herein may be combined with one or more clinical indicia relevant to the patient population including, but not limited to, demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more renal biomarker assay measurements are described hereinafter. In: Harrison's Principles of Internal Medicine, 17th Ed., McGraw Hill, New York, pages 1741-1830; and In: Current Medical Diagnosis & Treatment 2008, 47th Ed, McGraw Hill, New York, pages 785-815, each of which are herein incorporated by reference in their entirety.

When more than one biomarker is measured, the individual biomarkers may be measured in samples obtained at the same time, or may be determined from samples obtained at different (e.g., an earlier or later) times. The individual biomarkers may also be measured on the same or different body fluid samples. For example, one renal biomarker may be measured in a serum or plasma sample and another renal biomarker may be measured in a urine sample. In addition, assignment of a likelihood may combine a renal biomarker assay measurement with temporal changes in one or more additional variables.

B. Detectable Labels

Generation of a detectable signal from the detectable label can be performed using various optical, acoustical, and electrochemical methods. Examples of detection modes include, but are not limited to, fluorescence, radiochemical detection, reflectance, absorbance, amperometry, conductance, impedance, interferometry, ellipsometry, etc. In certain of these methods, the solid phase antibody may be coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

Biological assays require methods for detection, and one of the most common methods for quantitation of assay measurements is to conjugate a detectable label to a protein or nucleic acid that has affinity for one of the components in the biological system being studied. Detectable labels used in the immunoassays described above may include, but are not limited to, molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents may involve at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups and are believed to react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

C. Hyaluronic Acid Assays

Urinary hyaluronic acid may be determined by first collecting voided (clean-catch) urine specimens that are stored at −20° C. until assayed. The HA assay may be based upon an ELISA plate based assay for hyaluronan using biotinylated proteoglycan G1 domain (HA-binding) region. Fosang et al. Matrix, 10:306-313 (1990). In one embodiment, the assay may be modified by using a 96-well microtiter plates coated with human umbilical cord HA (25 µg/ml) that are incubated with serial dilutions of urine specimens in phosphate buffer saline (PBS)+0.05% Tween 20 (PBS+Tween), and a biotinylated bovine nasal cartilage HA-binding protein (1 µg/ml). Following incubation at room temperature for 16 h, the wells were washed in PBS+Tween. The HA binding protein bound to these wells was quantitated using an avidin-biotin detection system and ABTS (2,2' azino-bis(3-ethyl-benzthiazolin-6-sulfonic acid)) substrate (Vector Laboratories, Burlingame, Calif.). A standard graph can be prepared by plotting absorbance (405 nm) versus human umbilical cord HA concentrations (ng/ml). Using this graph, the HA concentration in each dilution of the urine specimen may be calculated. From several such determinations, the mean HA concentration in each sample was determined and then normalized to the creatinine concentration (mg/ml) in the urine sample.

The above described HA assay of the invention has been shown to detest bladder cancer at a sensitivity of about 88% using a cut-off limit of approximately 500 ng/ml. Lokeshwar, et al. Methods for detection and evaluation of bladder cancer U.S. Pat. No. 6,350,571 (herein incorporated by reference). Although it is not necessary to understand the mechanism of an invention, it is believed that cut-off limits of HA concentration may vary, and the population spread must be taken into consideration. Setting the cut-off limit of HA concentration to arrive at appropriate predictors for long-term dialysis may involve considering factors including, but not limited to, age, diet, concentration of protein in the sample, environmental influence, genetic background, hydration status, medical history, physical condition, sex, weight, or the like.

In one embodiment, the HA assay comprises adsorbing HA onto the surface of a solid phase. Although it is not necessary to understand the mechanism of an invention, it is believed that the HA can be derived from any convenient source, such as human umbilical cord. The solid phase can be any conventional solid phase, including nitrocellulose and the like, and preferably microtiter wells. After adsorbing HA onto the solid phase, the surface of the solid phase is preferably washed using conventional buffer(s). Because the solid phase still has sites left on its surface which are capable of coupling with the HA or other molecules, it is preferred that prior to addition of the sample a blocking substance be added so as to cover any part of the solid phase on which the HA has not been adsorbed. Examples of suitable blocking substances include γ-globulin and albumin derived from cows or other animals. Bovine serum albumin is preferred. After blocking the free sites of the solid phase, the surface of the solid phase is preferably washed using conventional buffer(s).

Next, HA binding protein (HABP) is added to the coated solid support in the presence of a sample of biological fluid collected from a person suspected of having a kidney injury, and incubated under conditions such that the HABP is permitted to bind to the HA coated on the solid support and the urinary HA (if any is present). The incubation time and conditions can vary within wide limits, but an incubation time of about 4 to about 16 hours, and an incubation temperature of about 4° C. to about 37° C. is satisfactory. Nonetheless, longer or shorter incubation times and higher or lower incubation temperatures are also possible.

HABP suitable for use with the assays of this invention can be readily purified from a number of sources, such as bovine nasal cartilage (Tengblad, Biochim. Biophys. Acta, 578: 281-289, 1979), pig laryngal cartilage (Fosang et al., Matrix, 10: 306-313, 1990). After binding of the HABP to the coated HA and/or the sample HA, the surface of the solid phase is preferably washed using conventional buffer(s). Next, the amount of HABP bound to the HA coated on the solid support is determined. Preferably, the HABP is biotinylated, and the bound HABP is visualized following incubation with an avidin-enzyme conjugate and any substrate for the enzyme which generates a colored product. Such a detection system does not use radioactivity as a label, multiple markers (i.e., enzyme molecules) are immobilized for every HABP bound to the solid support, and the signal (i.e., colored product) is amplified through turnover of the enzyme. However, any conventional marker system may be used in conjunction with the HABP.

Examples of suitable marker systems include enzymes, fluorescence, chemiluminescence, enzyme-substrate, isotope markers, radiolabels and the like. Preferably, the determination of the amount of HABP bound to the HA coated on the solid support is via an avidin-biotin detection system. Another useful marker system employs keratin sulfate and keratin sulfate-reactive antibodies. The urinary HA levels can usefully be determined using a microtiter plate reader, and can be extrapolated from a standard graph. The amount of HABP coupled with the coated HA can then be correlated with the existence of bladder cancer in the patient from whom the sample of biological fluid was collected.

For the HA assay, purified hyaluronic acid is preferably used as a standard.

The HA-binding fragments used in the above assay may be isolated from human umbilical cord HA (.about.500 mg) by digestion with 20,000 units of testicular hyaluronidase (Sigma Chemical Co., St. Louis, Mo.), at 37° C. for different time intervals. The HA fragments generated were separated on a Sephadex G-50 column (1.5×120 cm). Ten ml fractions were collected and assayed for the uronic acid content (Bitter and Muir, A modified uronic acid carbazole reaction. Anal. Biochem., 4:330-334, 1962). The fractions were combined to give three preparations, F1, F2 and F3. The number of reducing ends in each fraction was determined by the Dygert assay (Dygert et al., Determination of reducing sugars with improved precision. Anal. Biochem., 13: 367-374, 1965). Since each linear polysaccharide of HA or its fragment contains a single reducing end, the chain length of each fragment was calculated from the number of reducing ends per mole of uronic acid. The size range of oligosaccharides in each fraction was also determined by incorporating $^3$H labeled HA (prepared as described in Lokeshwar et al., Ankyrin binding domain of CD44(GP85) is required for the expression of hyaluronic acid-mediated adhesion function. J. Cell Biol., 126 1099-1109, 1994) during HA digestion and analyzing the fragments by gel electrophoresis and fluorography.

Accordingly, in one embodiment of this invention long-term dialysis may be predicted by quantitatively measuring HA in a sample of biological fluid (such as, for instance, a urine specimen) collected from a patient suspected of having a kidney injury and/or disease. Any conventional assay methodology can be used to determine the presence and measurement of HA, including radioassays, sandwich assays, inhibition assays and the like. However, HA is preferably measured a competitive binding assay. More preferably, the assay of the invention works in the same manner as an ELISA test, but does not make use of antibody completing mechanisms.

In one embodiment, long-term dialysis can be predicted using a method, comprising:
(a) coating a solid support (preferably, microtiter wells) with HA;
(b) contacting and incubating HA binding protein (HABP) with the coated solid support in the presence of a sample of biological fluid (such as a urine sample) collected from a person suspected of having a kidney injury and/or disease, under conditions such that the HABP is permitted to bind to the HA coated on the solid support and the HA in the sample (if any is present);
(c) determining the amount of HABP bound to the HA coated on the solid support, and determining therefrom the amount of HA present in the sample.

Although it is not necessary to understand the mechanism of an invention, it is believed that when HA is present in the sample, less HABP will bind to the coated HA, as determined by, for instance, comparison with a standard. In other words, a reduction in the amount HABP bound to the coated HA (i.e., as compared to the controls) would mean elevated HA present in the sample. In one embodiment, elevated urinary HA is predictive of long-term dialysis.

In one embodiment, the method may further comprise detecting a signal associated with, or produced by, the bound HABP. Although it is not necessary to understand the mechanism of an invention, it is believed that the amount of HABP bound to the HA coated on the solid support may be used to determine therefrom the amount of HA present in the sample. For example, a microtiter plate reader can be used to measure absorbance of colored product as an indirect measure of biotinylated HABP bound to the solid support (e.g., an avidin-enzyme conjugate and labeled substrate are used to generate the colored product). The maximum absorbance can be obtained by incubating the HA-coated wells with buffer alone in the absence of any HA or HA-containing sample. A standard graph can then be prepared by plotting absorbance versus ng/well or 0.2 ml of HA. Using this standard graph, the HA concentration (ng/ml) in each dilution of the sample can be calculated. From several such determinations the mean HA concentration in each sample can be determined. Creatinine concentration can be determined such that the HA concentrations can be normalized.

In one embodiment, predicting whether a patient will required long-term dialysis may be determined by the following calculations derived from normalized urinary HA level: HA (ng/ml) extrapolated from a time course graph× dilution factor/mg/ml urinary protein. For example, a low absorbance reading would be indicative of a significant amount of HA in the urine sample, which would itself be indicative of the need for long-term dialysis in the patient.

1. Isolation of HA and HA Fragments from Patient Urine

Urine specimens from normal subjects and patients may be concentrated 10-fold and dialyzed extensively against PBS. Approximately 2 ml of each of the dialyzed specimens (about 0.20 mg protein) was applied to a Sepharose 6 CL-B column (1.5×120 cm) (Pharmacia, Piscataway, N.J.) equilibrated with PBS. The column was run in PBS at 7 ml/hr and 3.5 ml fractions were collected. The fractions were assayed for HA by the ELISA-like assay as described above. Since the standard globular protein markers and linear polysaccharides such as HA and HA fragments have different shapes, the column was calibrated using human umbilical vein HA (Mr.about.2×$10^6$ D) and the HA fragments, F1, F2 and F3.

The ELISA-like assay, may involve the use of a biotinylated HA binding protein to determine the HA concentration in urine specimens. Because urinary HA levels (i.e., normally in ng quantities) are found to be influenced by the hydration status and urine output, these levels were normalized to urinary creatinine content.

D. Assay Correlations

In some embodiments, the renal biomarker assay measurement is/are correlated to one or more future changes in renal function. In one embodiment, risk stratification comprises determining a subject's likelihood (i.e., for example, probability) for a future improvement in renal function.

In one embodiment, the renal biomarker assay measurement is/are correlated to a likelihood of such a future improvement in renal function. In one embodiment, the method correlates a likelihood of such a future injury to renal function. In one embodiment, the risk stratification comprises determining a subject's risk for progression to acute renal failure (ARF).

In one embodiment, the renal biomarker assay measurement is/are correlated to a likelihood of such progression to acute renal failure (ARF). In one embodiment, the risk stratification method comprises determining a subject's outcome risk.

In one embodiment, the assay measurement is/are correlated to a likelihood of the occurrence of a clinical outcome related to a renal injury suffered by the subject.

Consequently, the measured concentration value(s) may each be compared to a threshold value, wherein either a "positive going kidney injury marker", or a "negative going kidney injury marker" is identified. In one embodiment, the risk stratification comprises determining a subject's risk for future reduced renal function. In some embodiments, the method assigns a likelihood, risk, or probability that such that an event of interest is more or less likely to occur within 180 Days of the time at which the body fluid sample is obtained from the subject. In some embodiments, the assigned likelihood, risk, or probability relates to an event of interest occurring within a time period including, but not limited to, 18 months, 120 Days, 90 Days, 60 Days, 45 Days, 30 Days, 21 Days, 14 Days, 7 Days, 5 Days, 96 hours, 72 hours, 48 hours, 36 hours, 24 hours, 12 hours, or less. Alternatively, assigning a risk at 0 hours of the time at which the body fluid sample is obtained from the subject is equivalent to diagnosis of a current condition.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, a cost/benefit analysis is involved in selecting a diagnostic threshold.

1. Thresholds

Suitable thresholds may be determined in a variety of ways. For example, one recommended diagnostic threshold for the diagnosis of acute myocardial infarction uses cardiac troponin, wherein the diagnostic threshold is set at the 97.5th percentile of the cardiac troponin concentration measured in a normal population. Another method to determine a diagnostic threshold comprises measuring serial samples from the same patient, where a prior "baseline" result is used to monitor for temporal changes in a biomarker level.

Population studies may also be used to select thresholds. For example, Reciever Operating Characteristic ("ROC") arose from the field of signal detection theory developed during World War II for the analysis of radar images, and ROC analysis is often used to select a threshold to distinguish a "diseased" subpopulation from a "nondiseased" subpopulation. Predictive power balances the occurrences of false positives (i.e., for example, when the person tests positive, but actually does not have the disease) and false negatives (i.e., for example, when the person tests negative, suggesting they are healthy, when they actually do have the disease). To draw a ROC curve, the true positive rate (TPR) and false positive rate (FPR) are determined as the decision threshold is varied continuously. Since TPR is equivalent with sensitivity and FPR is equal to (1-specificity), the ROC graph is sometimes called the sensitivity vs (1-specificity) plot. A perfect test will have an area under the ROC curve of 1.0; a random test will have an area of 0.5. A threshold value is selected to provide an acceptable level of specificity and sensitivity usually determined by summing specificity values with sensitivity values. Consequently, the larger the calculated threshold value the greater the prediective power of the specific assay measurement under analysis.

In this context, "diseased" is meant to refer to a population having one characteristic (i.e., for example, the presence of a disease or condition or the occurrence of some outcome) and "nondiseased" population lacking the same characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold value comparisons, other methods for correlating assay measurements to a patient classification (i.e., for example, occurrence or nonoccurrence of disease, likelihood of an outcome, etc.) include, but are not limited to, decision trees, rule sets, Bayesian methods, and neural network methods. These methods can produce probability values representing the degree to which a subject or patient belongs to one classification out of a plurality of classifications.

Multiple thresholds may also be used to assess renal status in a subject and/or patient. For example, a multiple thresholding method may combine a "first" subpopulation which is predisposed to one or more future changes in renal status, the occurrence of an injury, a classification, etc., with a "second" subpopulation which is not so predisposed into a single group. This combination group is then subdivided into three or more equal parts (i.e., for example, tertiles, quartiles, quintiles, etc., depending on the number of subdivisions). An odds ratio is assigned to subjects based on which subdivision they fall into. If one considers a tertile embodiment, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

2. Specificity and Sensitivity

In some embodiments, a measured concentration of one or more renal biomarkers, or a composite of such biomarkers, may be treated as continuous variables. For example, any particular biomarker concentration can be converted into a corresponding probability of a future reduction in renal function for the subject, the occurrence of an injury, a classification, etc. Alternatively, a threshold value can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed.

In one embodiment, a threshold value is selected to separate a first and a second population by one or more of the following measures of test accuracy:

i) an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

ii) a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

iii) a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

iv) at least about 75% sensitivity, combined with at least about 75% specificity; a positive likelihood ratio (calculated as sensitivity/(1-specificity)) of greater than 1, at least about 2, more preferably at least about 3, still more preferably at least about 5, and most preferably at least about 10; or v) a negative likelihood ratio (calculated as (1-sensitivity)/specificity) of less than 1, less than or equal to about 0.5, more preferably less than or equal to about 0.3, and most preferably less than or equal to about 0.1.

Various measures of test accuracy have been reported and used to determine the effectiveness of a given biomarker. Fischer et al., *Intensive Care Med.* 29:1043-1051 (2003). These accuracy measures include, but are not limited to, sensitivity and specificity, predictive values, likelihood ratios, diagnostic odds ratios, and AUC ROC values. For example, AUC ROC values are equal to the probability that a classifier will rank a randomly chosen positive instance higher than a randomly chosen negative one. Consequently, an AUC ROC value may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1.

E. Clinical Indicia Assays

Additional clinical indicia may be combined with the renal biomarker assay measurement of the present invention to improve the sensitivity and the specificity of the correlations to risk stratification, classification, diagnosis, and/or prognosis of a renal injury and/or disease. These include, but are not limited to other biomarkers related to renal status.

Examples which recite the common biomarker name, followed by the Swiss-Prot entry number for that biomarker or its parent, include but are not limited to: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Cadherin-3 (P07858); Ceruloplasmin (P00450); Clusterin (P10909); Complement C3 (P01024); Cysteine-rich protein (CYR61, 000622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

1. Risk Stratification Improvements

For purposes of risk stratification clinical indicia biomarker that improve determining renal status include but are not limited to: Adiponectin (Q15848); Alkaline phosphatase (P05186); Aminopeptidase N (P15144); CalbindinD28k (P05937); Cystatin C (P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, 000458); Isovaleryl-CoA dehydrogenase (IVD, P26440); I-TAC/CXCL11 (O14625); Keratin 19 (P08727); Kim-1 (Hepatitis A virus cellular receptor 1, 043656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, 015244); Osteoprotegerin (O14788); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-11, P20333); Tissue inhibitor of metalloproteinases 3 (TIMP-3, P35625); uPAR (Q03405) may be combined with the kidney injury marker assay measurement of the present invention.

F. Demographic Information Indicia

Other clinical indicia which may be combined with the renal biiomarker measurements of the present invention includes demographic information including but not limited to weight, sex, age, race, medical history, family history, type of surgery, pre-existing diseases such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay measurement are described hereinafter. In: Harrison's Principles of Internal Medicine, 17th Ed., McGraw Hill, New York, pages 1741-1830; and In: Current Medical Diagnosis & Treatment 2008, 47th Ed, McGraw Hill, New York, pages 785-815, each of which are hereby incorporated by reference in their entirety.

Combining renal biomarker measurements with clinical indicia measurements in this manner can comprise the use of multivariate logistical regression, loglinear modeling, neural network analysis, n-of-m analysis, decision tree analysis, etc. This list is not meant to be limiting.

G. Conventional Renal Diagnostics

As noted above, the terms "acute renal (or kidney) injury" and "acute renal (or kidney) failure" as used herein are generally defined, in part, in terms of changes in serum creatinine from a baseline value. Most conventional definitions of ARF have common elements, including but not limited to the use of serum creatinine and, often, urine output. Patients may present with renal dysfunction without an available baseline measure of renal function for use in this comparison. In such an event, one may estimate a baseline serum creatinine value by assuming the patient initially had a normal GFR.

1. Glomerular Filtration Rate and Creatinine

Glomerular filtration rate (GFR) is generally defnided as the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

By normalizing the GFR to the body surface area, a GFR of approximately 75-100 ml/min per 1.73 m² can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration (UCr), urine flow rate (V), and creatinine's plasma concentration (PCr) are known. Since the product of urine concentration and urine flow rate yields creatinine's excretion rate, creatinine clearance is also said to be its excretion rate (UCr×V) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m². While most adults have a BSA that approaches 1.7 (1.6-1.9), extremely obese or slim patients should have their CCr corrected for their actual BSA:

$$C_{Cr\text{-corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a mL/kg/hr basis, hourly urine collection and measurement is adequate. In the case where, for example, only a cumulative 24-h output was available and no patient weights are provided, minor modifications of the RIFLE urine output criteria have been described. For example, some have assumed an average patient weight of 70 kg, wherein patients are assigned a RIFLE classification based on the following: <35 mL/h (Risk), <21 mL/h (Injury) or <4 mL/h (Failure). Bagshaw et al., *Nephrol. Dial. Transplant.* 23:1203-1210 (2008).

2. Treatment Regimen Selection

Once a renal diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. Various appropriate treatments for numerous diseases have been previously discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the renal biomarkers of the present invention may be used to monitor a course of treatment. For example, an improved prognostic state or a worsened prognostic state may indicate that a particular treatment is or is not efficacious.

IV. Antibodies

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In some embodiments, antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity may be calculated as $K_d = k_{off}/k_{on}$ ($k_{off}$ is the dissociation rate constant, $K_{on}$ is the association rate constant and Kd is the equilibrium constant). Affinity can be determined at equilibrium by measuring the fraction bound (r) of labeled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecules By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12:425-443 (1991); and Nelson et al., *Comput. Methods Programs Biomed.* 27: 65-68 (1988).

Numerous publications discuss the use of phage display technology to produce and screen libraries of polypeptides for binding to a selected analyte. See, e.g, Cwirla et al., *Proc. Natl. Acad. Sci. USA* 87: 6378-6382 (1990); Devlin et al., *Science* 249:404-406 (1990); Scott et al., *Science* 249:386-388 (1990); and Ladner et al., U.S. Pat. No. 5,571,698 (all references herein incorporated by reference). A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

Antibodies generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

Antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

V. Kits

In some embodiments, the present invention also contemplates devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

In some embodiments, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

In one embodiment, the invention contemplates to diagnostic kits for predicting long-term dialysis. In one embodiment, the kit comprises HA and/or HAase, HABP and a marker or HABP conjugated to a marker, and ancillary reagents suitable for use in detecting the presence of HA and/or HAase in a biological sample (i.e., for example, a urine sample). An example of a diagnostic kit contemplated by this invention is a conventional dipstick test device.

In one embodiment, a dipstick test device may support an HA assay to predict long-term dialysis. For example, using conventional methodology a solid phase in the form of a dipstick can be used to assay HA, as described above. In one embodiment, the dipstick can be coated or impregnated with HA, wherein the dipstick may be used to test any biological fluid, including but not limited to urine.

EXPERIMENTAL

In some embodiments, the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Normalized Hyaluronic Acid in Human Urine Samples

Hyaluronic acid was determined in human urine as described above. A time course was generated by collecting and analyzing HA in urine for two weeks (i.e., fourteen Days; D1-D14). The data presented shows recovering patients and non-recovering patients at twenty-eight (28) Days after suffering a kidney injury. (i.e., for example, R28=recovering patients; and NR28=non-recovering patients). During the fourteen (14) Day collection period samples were analyzed on Day 1 (D1), Day 7 (D7), and Day 14 (D14). See, FIG. 1.

The data demonstrates that for recovering patients, hyaluronic acid was highest on D1 and progressively decreased on D7 and D14. In contrast, for non-recovering patients, hyaluronic acid steadily increased over the same time period. Clearly, the data suggests that hyaluronic acid correlates with recovery from a kidney injury.

Example 2

Absolute Normalized Hyaluronic Acid Levels in Human Urine Samples

The data in this example examines the differences between the normalized absolute hyaluronic acid levels above samples taken on D1, D7, and/or D14 after kidney injury collected in accordance with Example 1 for patients showing recovery at both twenty-eight Days (R28) and sixty Days (R60) past kidney injury, and non-recovering patients (NR28 and NR60).

Figure 2:
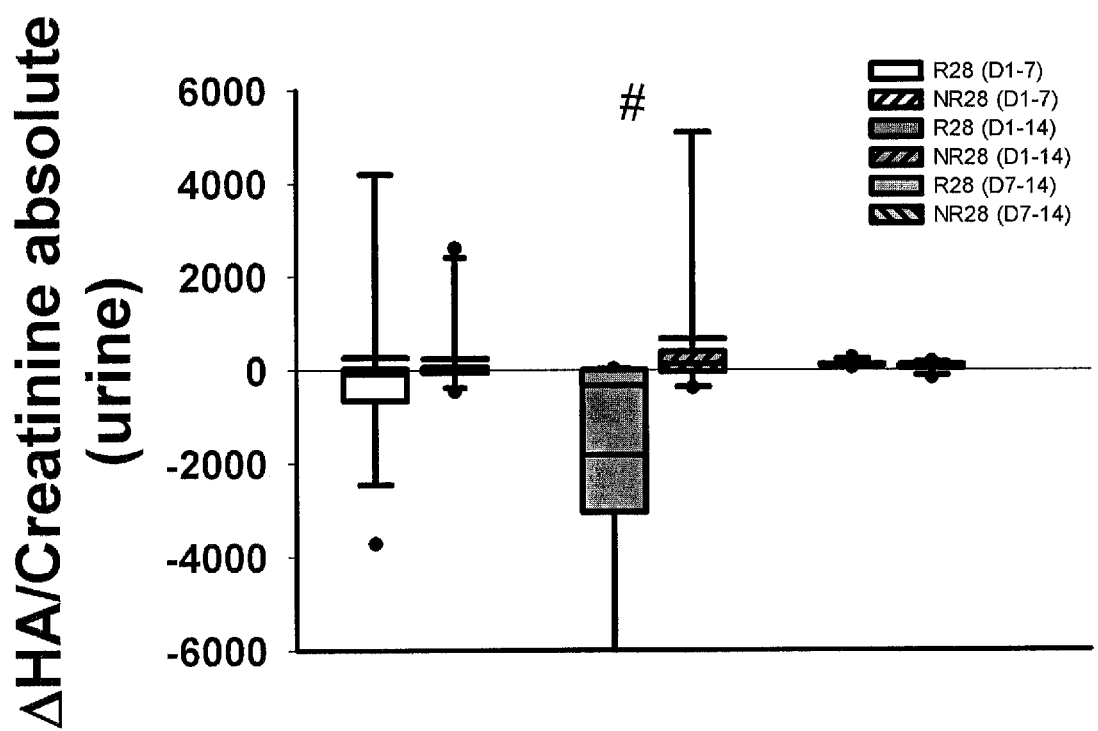
FIG. 2 presents exemplary data showing absolute differences between urine samples taken on D1, D7 and/or D14 from patients either recovering or not recovering twenty-eight Days after kidney injury (R28 and NR28, respectively).
Figure 3:
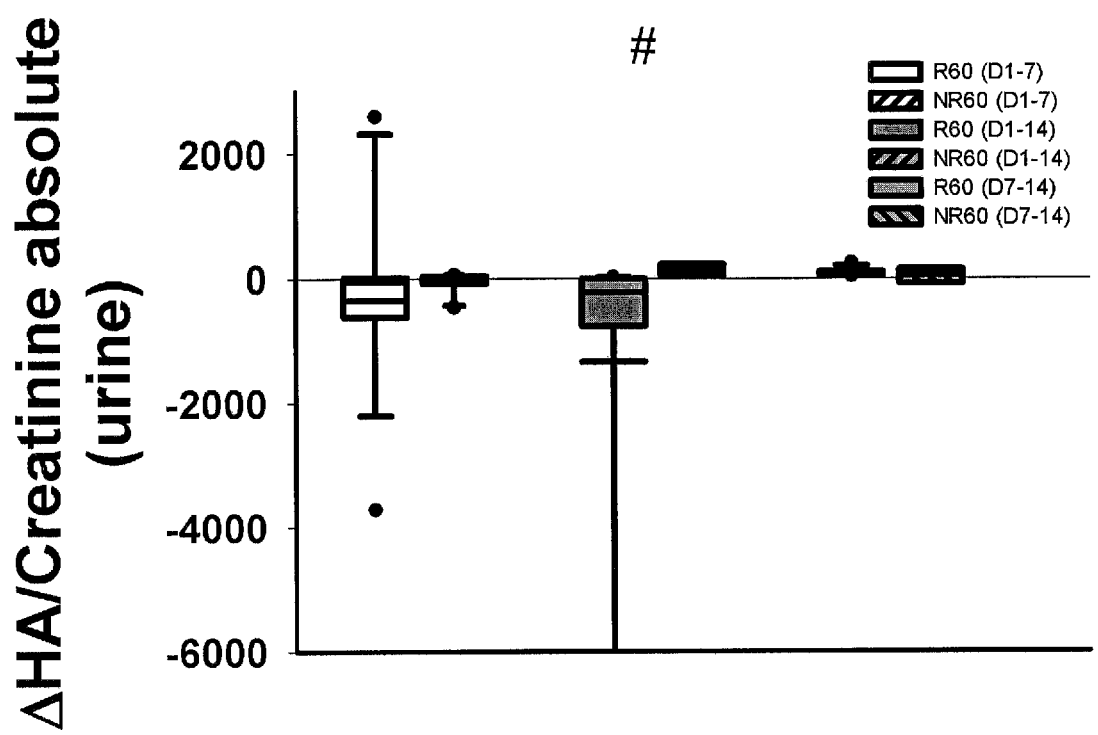
FIG. 3 presents exemplary data showing absolute differences between urine samples taken on D1, D7 and/or D14 from patients either recovering or not recovering sixty Days after kidney injury (R60 and NR60, respectively).
Figure 4:
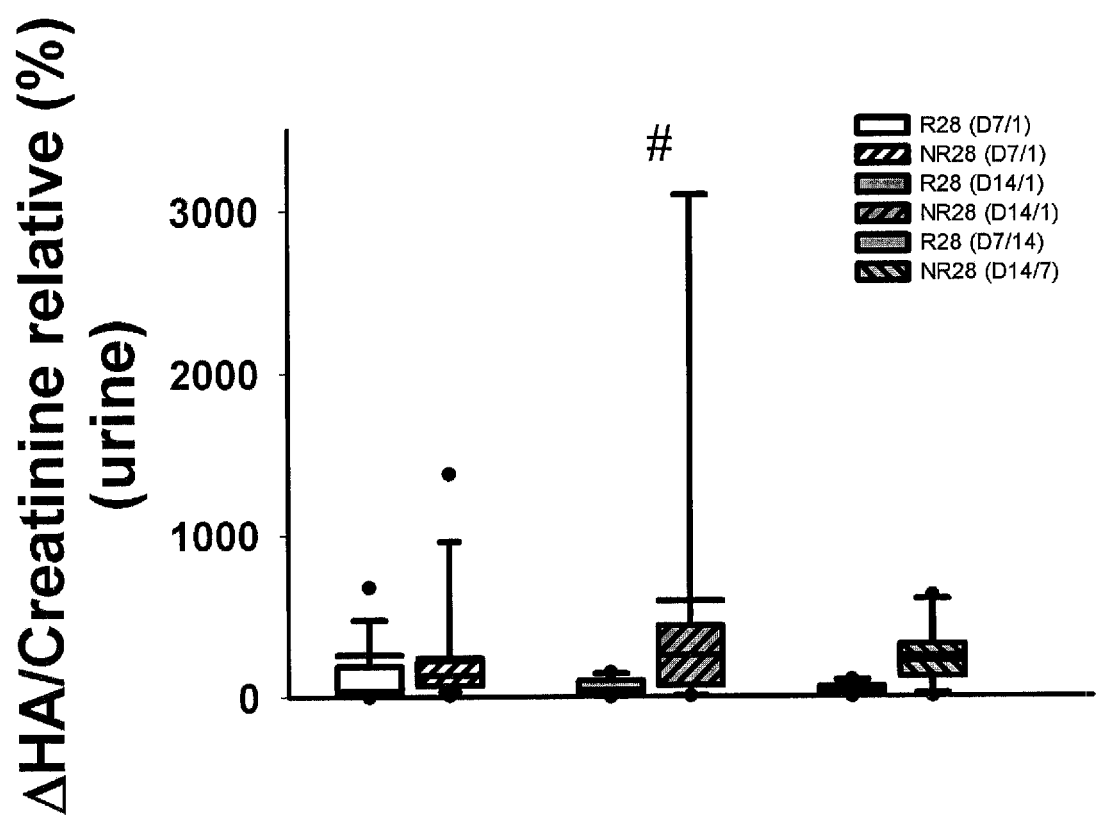
FIG. 4 presents exemplary data showing relative differences between urine samples taken on D1, D7 and/or D14 from patients either recovering or not recovering twenty-eight Days after kidney injury (R28 and NR28, respectively).

The data show that between Day 1 & Day 7, as well as between Day 1 & Day 14, the recovering patients demonstrated clear reductions in excretion of normalized hyaluronic acid (i.e., for example, absolute hyaluronic acid excretion decreased over this time period). The difference between Day 7 & Day 14 was, however, negligible meaning that the excretion rate was unchanged. In contrast, in non-recovering patients the difference between Day 1 & Day 7, as well as between Day 1 & Day 14 demonstrated clear increases in the excretion of normalized hyaluronic acid (i.e., for example, absolute hyaluronic acid excretion increased over this time period). Also, the excretion rate did not change between Day 7 & 14. See, FIGS. 2 and 3.

Example 3

Relative Normalized Hyaluronic Acid Levels in Human Urine Samples

This example replots the data in accordance with Example 2 to further illustrate the magnitude of the differences between recovering patients and non-recovering patients. In particular, the data is expressed as a percentage (i.e., D7÷D1, D14÷D1, D7÷D14, or D14÷D7).

The data show that in recovering patients that the relative hylauronic acid excretion progressively decreases between Day 1 and Day 14, where the relative difference between Day 14 and Day 7 is almost negligible. This is consistent with the interpretation of the above data suggesting that hyaluronic acid decreases in recovering kidney injury patients over time. In contrast, the data shows that in non-recovering patients the relative hyaluronic acid excretion remained elevated throughout the time period. This is consistent with the interpretation of the above data suggesting that hyaluronic is elevated in non-recovering kidney injury patients over time. See, Figures, 4 and 5.

Example 4

Prediction of Long-Term Dialysis at D14 Following Kidney Injury

Figure 6:
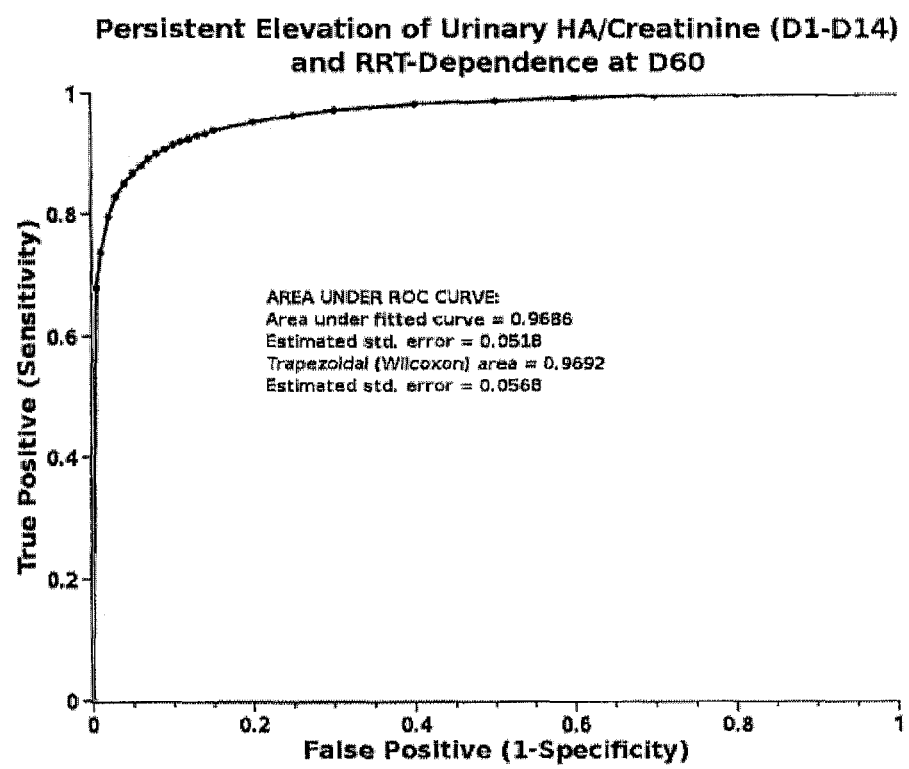
FIG. 6 presents exemplary data showing the high sensitivity of predicting dialysis in patients sixty Days after kidney injury, when HA excretion was persistently elevated between D1 and D14.

The data presented in accordance with Example 2 was analyzed and replotted to evaluate the relationship between True Positives and False Positives. In particular, under conditions where there was a persistent elevation of urinary HA/creatinine (i.e., the difference between D1 and D14 measurements) there was a high sensitivity to predicting that the patient would be on long-term dialysis on D60 after kidney injury. See, FIG. 6. In conclusion, the data suggest that in patients demonstrating persistently elevated urinary HA between D1-D14 after kidney injury will be on dialysis on (and most likely after) D60.

Example V

TGF-β1 Predicts Post-AKI Renal Recovery

This study was ancillary to a larger multicenter randomized controlled trial studying the effect of different renal replacement therapy doses on survival from AKI that included 24 patients.

Figure 7:
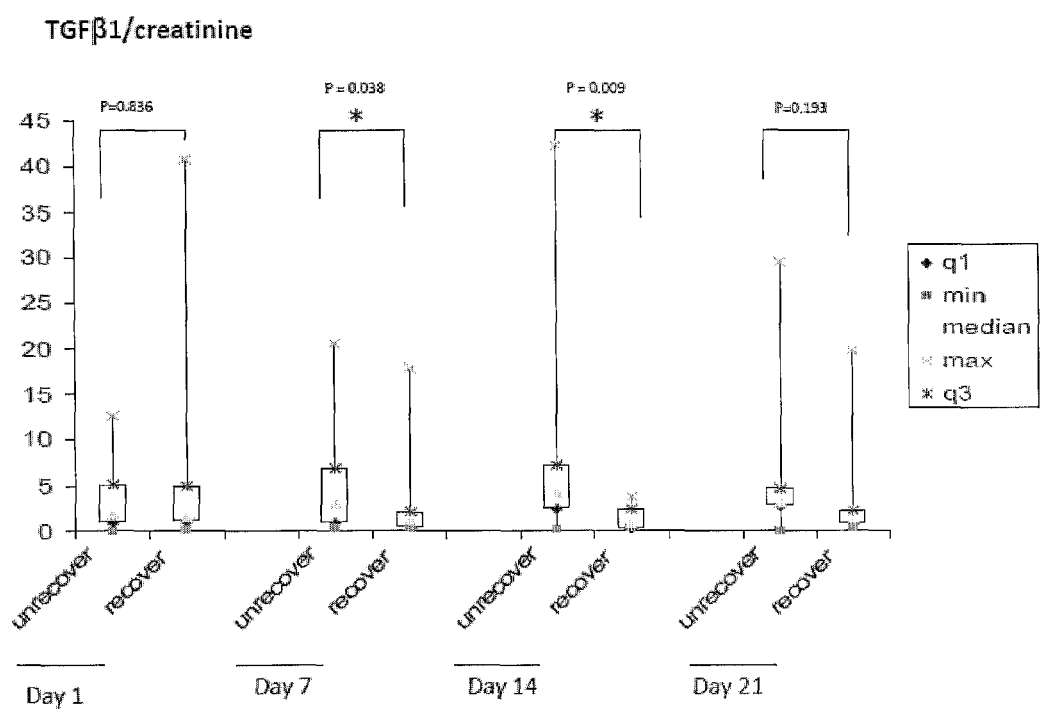
FIG. 7 presents exemplary data showing urinary TGF-β1/creatinine ratio data during the first twenty-one Days after onset of an AKI. Ratios were significantly higher in non-recovering patients on both Day 7 and Day 14.

Urinary TGF-β1 was significantly greater at Day 14 after onset of AKI in patients that failed to recover renal function by Day 60 as compared to those who did recover (p<0.01). See, FIG. 7.

Urinary TGF-β1 values predicted renal recovery by Day 60, using samples collected at Day 14 after AKI onset and having an Area Under the Receiver Operator Characteristic Curve (AUC ROC) of 0.81 (estimated std. error=0.09). Furthermore, if one considers the change in urinary TGF-β1, from Day 1 to Day 14, the area under the AUC ROC curve increases to 0.84 (p<0.01). TGF-b1 was measured using a commercially available ELISA kit (R&D Systems, Minneapolis, Minn.).

Example VI

Death Receptor 5 (DR5) Predicts Post-AKI Renal Recovery

This study was ancillary to a larger multicenter randomized controlled trial studying the effect of different renal replacement therapy doses on survival from AKI included 25 subjects.

Urinary DR5 was significantly greater at Day 14 after onset of AKI in subjects that failed to recover renal function by Day 60 as compared to those who did recover. See, Table 6.

TABLE 6

DR5 values for recoverers and non-recoverers of renal function by Day 60. (A) Mean DR5 values displayed for Days 1 and 14, non-recoverers and recoverers. (B) Mean log DR5 values displayed for Days 1 and 14, non-recoverers and recoverers.

| A | MEAN DR5 VALUES | | |
|---|---|---|---|
| Day | N | non-recoverers | recoverers |
| 1 | 25 | 137.1 | 60.42 |
| 14 | 14 | 506.0 | 59.27 |
| B | MEAN log DR5 VALUES | | |
| Day | N | non-recoverers | recoverers |
| 1 | 25 | 3.21 | 2.984 |
| 14 | 14 | 4.5 | 2.411 |

Urinary DR5 values predicted renal recovery by Day 60, using samples collected at Day 14 after AKI onset and having an Area Under the Receiver Operator Characteristic Curve (AUC ROC) of 0.90 (p<0.02). DR5 was measured using a commercially available test kit (Invitrogen, Carlsbad, Calif.). The assay system is based upon an extracellular Luminex® bead platform that was multiplexed with inflammatory cytokine 5-plex, +IL-10, TNF-$R_1$, and TNF-$R_2$.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for predicting dialysis independence after an acute renal injury, comprising:
    a) initiating renal replacement therapy in a patient having an acute renal injury, wherein said patient does not have an end stage renal disease;
    b) collecting at least two urine samples from said patient within fourteen days of said initiating renal replacement therapy;
    c) introducing said at least two urine samples into an assay device that detects a hyaluronic acid value normalized to urinary creatinine content in said urine sample, wherein said hyaluronic acid level decreases between an earlier urine sample hyaluronic acid value and a later urine sample hyaluronic acid level; and
    d) calculating therefrom an area under the curve receiver operated characteristic (AUC ROC) determination patient value between said earlier and later urine sample hyaluonic acid levels;
    e) correlating said AUC ROC patient value to an AUC ROC predetermined threshold value to determine a probability of recovery versus non-recovery for said patient;
    f) predicting a recovery of said patient when said probability of recovery vesus non-recovery correlates said AUC ROC patient value at or above said AUC ROC predetermined threshold value; and
    g) removing said patient from said renal replacement therapy under conditions of dialysis independence.

2. The method of claim 1, wherein said predicted probability of renal recovery versus non-recovery occurs within at least sixty Days from the onset of said acute renal injury.

3. The method of claim 1, wherein said sample is obtained within one Day from said initiation of renal replacement therapy.

4. The method of claim 1, wherein said predetermined threshold value comprises a urinary hyaluronic acid threshold value.

5. The method of claim 4, wherein said urinary hyaluronic acid threshold value is approximately 12 µg/mg of creatinine.

6. The method of claim 4, wherein said urinary hyaluronic acid threshold value comprises an area under the receiver operating characteristic curve (AUC ROC) value of at least 0.70.

7. The method of claim 1, wherein said predetermined threshold value comprises a hyaluronic acid threshold value and at least one clinical indicia threshold value.

8. The method of claim 7, wherein said urinary hyaluronic acid threshold value and said at least one clinical indicia threshold value comprises an area under the receiver operating characteristic curve (AUC ROC) value of at least 0.75.

9. The method of claim 1, wherein said predetermined threshold value comprises at least one clinical indicia threshold value.

10. The method of claim 1, wherein said patient value further comprises at least one clinical indicia value is selected from the group consisting of age, SOFA score, Charlson comorbidity index, and APACHE II score.

11. The method of claim 9, wherein said at least one clinical indicia threshold value comprises an area under the receiver operating characteristic curve (AUC ROC) value of at least 0.71.

12. The method of claim 1, wherein said patient value further comprises at least two patient clinical indicia values.

13. The method of claim 1, wherein said predetermined threshold value comprises at least two clinical indicia threshold values that comprises an area under the receiver operating characteristic curve (AUC ROC) value of at least 0.74.

14. The method of claim 12, wherein said at least two clinical indica values comprise an age value and a Charlson comorbidity index value.

* * * * *